United States Patent
Habash

(10) Patent No.: US 10,441,578 B2
(45) Date of Patent: Oct. 15, 2019

(54) ALTERING EXPRESSION LEVEL OF GLUTATHIONE S-TRANSFERASE GENES BY TREATING A HUMAN SUBJECT WITH A NITROXIDE

(71) Applicant: Louis Habash, Irvine, CA (US)

(72) Inventor: Louis Habash, Irvine, CA (US)

( * ) Notice: Subject to any disclaimer, the term of this patent is extended or adjusted under 35 U.S.C. 154(b) by 0 days.

(21) Appl. No.: 15/875,872

(22) Filed: Jan. 19, 2018

(65) Prior Publication Data

US 2019/0224178 A1 Jul. 25, 2019

(51) Int. Cl.
 *A61K 31/445* (2006.01)
(52) U.S. Cl.
 CPC .................. *A61K 31/445* (2013.01)
(58) Field of Classification Search
 CPC .................................................. A61K 31/445
 See application file for complete search history.

(56) References Cited

U.S. PATENT DOCUMENTS

2009/0017002 A1 1/2009 Gao et al.
2012/0046314 A1 2/2012 Habash et al.
2013/0344106 A1 12/2013 Nel et al.

FOREIGN PATENT DOCUMENTS

WO WO 2017/200953 A1 1/2009

OTHER PUBLICATIONS

Siriwardena, A.K. (aka Siri) World J. of Gastroenterol., 2014, vol. 20, No. 11, pp. 3033-3043.*
Stedzinski et al. Int. J. Pancreatol., 1995, vol. 18, No. 2, pp. 153-160 and/or Abstract.*
International Search Report and Written Opinion in related PCT/US2019/14313 dated Apr. 11, 2019.

* cited by examiner

*Primary Examiner* — Samira J Jean-Louis
(74) *Attorney, Agent, or Firm* — Knobbe Martens Olson & Bear, LLP

(57) ABSTRACT

A method of treatment is disclosed. The method comprises administering to a human subject, known to have decreased glutathione activity, an effective amount of a nitroxide antioxidant, wherein the nitroxide antioxidant increases an expression level of one or more genes encoding glutathione S-transferase enzymes, thereby increasing glutathione activity.

23 Claims, No Drawings

ALTERING EXPRESSION LEVEL OF GLUTATHIONE S-TRANSFERASE GENES BY TREATING A HUMAN SUBJECT WITH A NITROXIDE

BACKGROUND

Field

The present disclosure relates generally to the field of modulation of gene expression and more particularly to treating human subjects with a nitroxide antioxidant to alter gene expression.

Description of the Related Art

Genes generally encode biologically functional products. Gene expression describes transcription of gene encoding DNA sequences into complementary DNA (cDNA) and translation of cDNA into the functional products, such as proteins. Many factors, both internal and external, are involved in regulation of gene expression in cells. Such regulation can manifest in an adjustment of gene expression to increase or decrease a number of proteins made.

Diseases and conditions can be characterized by abnormal expression of one or more genes. Irregularities in gene expression underlie many diseases and conditions. Overexpression or underexpression of a gene or genes often results in dysfunction of downstream actions controlled by the same. Whether the gene is a regulator of cellular function or a vital in a responsive mechanism, modulation of the gene expression is a fundamental directive in addressing the foundational issues associated with many diseases and conditions.

Glutathione S-transferase (GST) gene family encodes genes that are critical for certain biological processes. Among other functions, GST genes are vital in the conjugation of glutathione (GSH) and various substrates within a cell for detoxification. Conjugation of GSH (e.g., by GST) with substrates such as xenobiotic compounds promotes enhanced excretion of the toxicity inducing substrate from the cell.

GSH is involved in cellular defense mechanisms and the metabolism of xenobiotic compounds. Conjugation with GSH can occur nonenzymatically or through the action of GST. Furthermore, activated metabolites produced from xenobiotic compounds by the action of mixed function oxygenase may also be conjugated with GSH.

SUMMARY

Some embodiments disclosed herein provide methods for increasing gene expression. The methods, in some embodiments, include identifying a human subject over the age of 35 and having a decrease expression level of a gene associated with glutathione S-transferase; and administering to the human subject an effective amount of a nitroxide antioxidant, resulting in an increased expression level of the gene. In some embodiments, the gene is selected from the group consisting of: Gstm3, Gstm6, Gsta3, Gstt1, Gsta4, Gstm1, Gstm4, Gstt2, Gstp1, and Gstk1. In some embodiments, the human subject is over the age of 45. In some embodiments, the human subject is over the age of 55. In some embodiments, the human subject is over the age of 65. In some embodiments, the expression level of the gene in a skin tissue is increased. In some embodiments, the expression level of the gene in an adipose tissue is increased. In some embodiments, the expression level of the gene in blood is increased. In some embodiments, the expression level of the gene in a neuronal tissue is increased. In some embodiments, the expression level of the gene in cardiac tissue is increased. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods for increasing the expression level of a gene in a human subject in need thereof, comprising: identifying a human subject having a decreased expression level of a gene associated with glutathione S-transferase; and administering to the human subject an effective amount of a nitroxide antioxidant, whereby the expression level of the gene associated with glutathione S-transferase is increased. In some embodiments, the gene is selected from the group consisting of: Gstm3, Gstm6, Gsta3, Gstt1, Gsta4, Gstm1, Gstm4, Gstt2, Gstp1, and Gstk1. In some embodiments, the decreased expression level of the gene is age-related. In some embodiments, the human subject is over the age of 35. In some embodiments, the human subject is over the age of 45. In some embodiments, the human subject is over the age of 55. In some embodiments, the human subject is over the age of 65. In some embodiments, the decreased expression level of the gene is disease-related. In some embodiments, the disease is selected from the group consisting of cancer, rheumatoid/osteoid arthritis, systemic lupus erythematosus (SLE), inflammatory bowel disease, Alzheimer's disease, multiple sclerosis, atherosclerosis, cardiovascular disease, cataracts, dementia, osteoporosis, type 2 diabetes, and hypertension. In some embodiments, the disease is age-related. In some embodiments, the expression level of the gene in a skin tissue is increased. In some embodiments, the expression level of the gene in an adipose tissue is increased. In some embodiments, the expression level of the gene in blood is increased. In some embodiments, the expression level of the gene in a neuronal tissue is increased. In some embodiments, the expression level of the gene in cardiac tissue is increased. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg.

In some embodiments, the effective amount of the nitroxide antioxidant is within a range of 15-30 mg/kg.

Some embodiments disclosed herein provide methods for reducing risk of a disease in a human subject in need thereof, comprising: identifying a human subject over the age of 35 having an increased risk of a disease due to a decreased expression level of a gene associated with glutathione S-transferase; and administering to the human subject an effective amount of a nitroxide antioxidant, whereby the expression level of the gene associated with glutathione S-transferase is increased. In some embodiments, the disease is selected from the group consisting of cancer, rheumatoid/osteoid arthritis, systemic lupus erythematosus (SLE), inflammatory bowel disease, Alzheimer's disease, multiple sclerosis, atherosclerosis, cardiovascular disease, cataracts, dementia, osteoporosis, type 2 diabetes, and hypertension. In some embodiments, the gene is selected from the group consisting of: Gstm3, Gstm6, Gsta3, Gstt1, Gsta4, Gstm1, Gstm4, Gstt2, Gstp1, and Gstk1. In some embodiments, the human subject is over the age of 45. In some embodiments, the human subject is over the age of 55. In some embodiments, the human subject is over the age of 65. In some embodiments, the expression level of the gene in a skin tissue is increased. In some embodiments, the expression level of the gene in an adipose tissue is increased. In some embodiments, the expression level of the gene in blood is increased. In some embodiments, the expression level of the gene in a neuronal tissue is increased. In some embodiments, the expression level of the gene in cardiac tissue is increased. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods comprising: identifying a human subject having or at risk of developing a cancer and in need of an increased expression level of a gene associated with glutathione S-transferase; and administering to the human subject an effective amount of a nitroxide antioxidant, whereby the expression level of the gene associated with glutathione S-transferase is increased. In some embodiments, the cancer can be selected from the group consisting of renal cell carcinoma bladder cancer, colorectal cancer, hepatocellular carcinoma, prostate carcinoma, and kidney carcinoma. In some embodiments, the gene is selected from the group consisting of: Gstm3, Gstm6, Gsta3, Gstt1, Gsta4, Gstm1, Gstm4, Gstt2, Gstp1, and Gstk1. In some embodiments, the cancer is age-related. In some embodiments, the human subject is over the age of 35. In some embodiments, the human subject is over the age of 45. In some embodiments, the human subject is over the age of 55. In some embodiments, the human subject is over the age of 65. In some embodiments, the expression level of the gene in a skin tissue is increased. In some embodiments, the expression level of the gene in an adipose tissue is increased. In some embodiments, the expression level of the gene in blood is increased. In some embodiments, the expression level of the gene in a neuronal tissue is increased. In some embodiments, the expression level of the gene in cardiac tissue is increased. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods comprising: identifying a human subject having or at risk of developing an autoimmune disease and in need of an increased expression level of a gene associated with glutathione S-transferase; and administering to the human subject an effective amount of a nitroxide antioxidant, wherein the expression level of the gene associated with glutathione S-transferase is increased. In some embodiments, the autoimmune disease can be selected from the group consisting of rheumatoid/osteoid arthritis, systemic lupus erythematosus (SLE), inflammatory bowel disease, multiple sclerosis, atherosclerosis, and osteoporosis. In some embodiments, the gene is selected from the group consisting of: Gstm3, Gstm6, Gsta3, Gstt1, Gsta4, Gstm1, Gstm4, Gstt2, Gstp1, and Gstk1. In some embodiments, the gene is Gstm3. In some embodiments, the autoimmune disease is age-related. In some embodiments, the human subject is over the age of 35. In some embodiments, the human subject is over the age of 45. In some embodiments, the human subject is over the age of 55. In some embodiments, the human subject is over the age of 65. In some embodiments, the expression level of the gene in a skin tissue is increased. In some embodiments, the expression level of the gene in an adipose tissue is increased. In some embodiments, the expression level of the gene in blood is increased. In some embodiments, the expression level of the gene in a neuronal tissue is increased. In some embodiments, the expression level of the gene in a cardiac tissue is increased. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods for a disease associated with a decreased apoptosis in a patient in need thereof, comprising: identifying a human subject having or at risk of developing a disease associated with a decreased expression of a gene associated with glutathione S-transferase; and administering to the human subject an effective amount of a nitroxide antioxidant, whereby the expression level of a gene associated with glutathione S-transferase is increased. In some embodiments, the disease can be selected from the group consisting of cancer, rheumatoid/osteoid arthritis, systemic lupus erythematosus (SLE), inflammatory bowel disease, Alzheimer's disease, multiple sclerosis, atherosclerosis, cardiovascular disease, cataracts, dementia, osteoporosis, type 2 diabetes, and hypertension. In some embodiments, the gene is selected from the group consisting of: Gstm3, Gstm6, Gsta3, Gstt1, Gsta4, Gstm1, Gstm4, Gstt2, Gstp1, and Gstk1. In some embodiments, the human subject is over the age of 35. In some embodiments, the human subject is over the age of 45. In some embodiments, the human subject is over the age of 55. In some embodiments, the human subject is over the age of 65. In some embodiments, the expression level of the gene in a skin tissue is increased. In some embodiments, the expression level of the gene in an adipose tissue is increased. In some embodiments, the expression level of the gene in blood is increased. In some embodiments, the expression level of the gene in a neuronal tissue is increased. In some embodiments, the expression level of the gene in a cardiac tissue is increased. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods for treating an individual in need thereof, comprising: identifying an individual over the age of 35 in need of an increased expression level of a gene associated with glutathione S-transferase; and administering to the individual an effective amount of a nitroxide antioxidant to increase the level of expression of the gene associated with glutathione S-transferase. In some embodiments, the gene is selected from the group consisting of: Gstm3, Gstm6, Gsta3, Gstt1, Gsta4, Gstm1, Gstm4, Gstt2, Gstp1, and Gstk1. In some embodiments, the human subject is over the age of 45. In some embodiments, the human subject is over the age of 55. In some embodiments, the human subject is over the age of 65. In some embodiments, the human subject has a decrease expression level of the gene. In some embodiments, the individual has or is at risk of developing an age-related condition. In some embodiments, the age-related condition comprises increased senescence in a tissue. In some embodiments, the age-related condition comprises inactivation of glutathione S-transferase in a tissue. In some embodiments, the age-related condition comprises increased molecular heterogeneity. In some embodiments, the age-related condition comprises increased functional impairment in a tissue. In some embodiments, the expression level of the gene in a skin tissue is increased. In some embodiments, the expression level of the gene in an adipose tissue is increased. In some embodiments, the expression level of the gene in blood is increased. In some embodiments, the expression level of the gene in a neuronal tissue is increased. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods for treating an individual in need thereof, comprising: identifying an individual having a disease-related decreased expression level of a gene associated with glutathione S-transferase; and administering to the individual an effective amount of a nitroxide antioxidant to increase the level of expression of the gene associated with glutathione S-transferase. In some embodiments, the disease can be selected from the group consisting of cancer, rheumatoid/osteoid arthritis, systemic lupus erythematosus (SLE), inflammatory bowel disease, Alzheimer's disease, multiple sclerosis, atherosclerosis, cardiovascular disease, cataracts, dementia, osteoporosis, type 2 diabetes, and hypertension. In some embodiments, the gene is selected from the group consisting of: Gstm3, Gstm6, Gsta3, Gstt1, Gsta4, Gstm1, Gstm4, Gstt2, Gstp1, and Gstk1. In some embodiments, the human subject is over the age of 35. In some embodiments, the human subject is over the age of 45. In some embodiments, the human subject is over the age of 55. In some embodiments, the human subject is over the age of 65. In some embodiments, the expression level of the gene in a skin tissue is increased. In some embodiments, the expression level of the gene in an adipose tissue is increased. In some embodiments, the expression level of the gene in blood is increased. In some embodiments, the expression level of the gene in a neuronal tissue is increased. In some embodiments, the expression level of the gene in a cardiac tissue is increased. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods for treating an individual having or at risk of developing a condition due to aging, comprising: identifying an individual over the age of 35; and administering to the individual an effective amount of a nitroxide antioxidant, whereby the expression level of the gene associated with glutathione S-transferase is increased. In some embodiments, the individual has a decreased expression level of the gene. In some embodiments, the gene is selected from the group consisting of: Gstm3, Gstm6, Gsta3, Gstt1, Gsta4, Gstm1, Gstm4, Gstt2, Gstp1, and Gstk1. In some embodiments, the condition is an age-related condition. In some embodiments, the age-related condition comprises increased senescence in a tissue. In some embodiments, the age-related condition comprises inactivation of glutathione S-transferase in a tissue. In some embodiments, the age-related condition comprises increased molecular heterogeneity. In some embodiments, the age-related condition comprises increased functional impairment in a tissue. In some embodiments, the age-related condition is selected from the group consisting of cancer, rheumatoid/osteoid arthritis, systemic lupus erythematosus (SLE), inflammatory bowel disease, Alzheimer's disease, multiple sclerosis, atherosclerosis, cardiovascular disease, cataracts, dementia, osteoporosis, type 2 diabetes, and hypertension. In some embodiments, the human subject is over the age of 35. In some embodiments, the human subject is over the age of 45. In some embodiments, the human subject is over the age of 55. In some embodiments, the human subject is over the age of 65.

Some embodiments disclosed herein provide methods for treatment, comprising administering to a human subject, known to have decreased glutathione activity, an effective amount of a nitroxide antioxidant, wherein the nitroxide antioxidant increases an expression level of one or more genes encoding glutathione S-transferase enzymes, thereby increasing glutathione activity. In some embodiments, the human subject is further known to have a disease in which the expression level of at least one gene selected from the group consisting of Gstm3, Gstm6, Gsta3, Gstt1, Gsta4, Gstm1, Gstm4, Gstt2, Gstp1, and Gstk1. In some embodiments, the nitroxide antioxidant is 4-hydroxy-2,2,6,6-tetramethylpiperidine-1-oxyl. In some embodiments, the nitroxide antioxidant increases GST enzymatic activity. In some embodiments, the disease is associated with (e.g., defined by) elevated cellular toxicity mediated by one or more xenobiotics. In some embodiments, the one or more genes are selected from a group consisting of Gstm3, Gstm6, Gsta3, Gstt1, Gsta4, Gstm1, Gstm4, Gstt2, Gstp1, and Gstk1.

Some embodiments disclosed herein provide methods for inhibiting development of a cancer, comprising administering to a human subject, known to be at risk of developing cancer mediated by decreased GSH activity (the activity of GSH as a reducing agent, or the GSH reducing activity), an effective amount of a nitroxide antioxidant, wherein GSH activity is increased, thereby inhibiting development of said cancer. In some embodiments, the human subject exhibits no outward symptoms of said cancer. In some embodiments, the human subject is not known to have said cancer. In some embodiments, the human subject is further known to have a decreased expression level of one or more genes selected from the group consisting of Gstm3, Gstm6, Gsta3, Gstt1, Gsta4, Gstm1, Gstm4, Gstt2, Gstp1, and Gstk1, and the treatment increases said expression level. In some embodiments, the nitroxide antioxidant is 4-hydroxy-2,2,6,6-tetramethylpiperidine-1-oxyl. In some embodiments, the nitroxide antioxidant increases enzyme mediated GSH activity.

Some embodiments disclosed herein provide methods for increasing the expression level of a gene in a human subject in need thereof, comprising identifying a human subject having a decreased expression level of a gene associated with GST activity, wherein the gene is selected from the group consisting of Gstm3, Gstm6, Gsta3, Gstt1, Gsta4, Gstm1, Gstm4, Gstt2, Gstp1, and Gstk1; and administering to the human subject an effective amount of a nitroxide antioxidant to increase the level of expression of the gene associated with GST. In some embodiments, the nitroxide antioxidant is 4-hydroxy-2,2,6,6-tetramethylpiperidine-1-oxyl. In some embodiments, the decreased expression level of the gene is age-related. In some embodiments, the decreased expression level of the gene is associated with cancer. In some embodiments, the decreased expression level of the gene is associated with a disease. In some embodiments, the decreased expression level of the gene is associated with a neurodegenerative disorder. In some embodiments, the decreased expression level of the gene is associated with an infection. In some embodiments, the decreased expression level of the gene is associated with an oxidative stress. In some embodiments, the expression level of the gene is reduced in a tissue selected from the group consisting of a skin tissue, an immune tissue, an adipose tissue, a pancreatic tissue, cardiac tissue, and a neuronal tissue.

Some embodiments disclosed herein provide methods for increasing an expression level, in a eukaryotic cell, of one or more genes encoding one or more GST enzymes by administering a nitroxide antioxidant to eukaryotic cell. In some embodiments, the one or more genes is selected from the group consisting of Gstm3, Gstm6, Gsta3, Gstt1, Gsta4, Gstm1, Gstm4, Gstt2, Gstp1, and Gstk1. In some embodiments, the nitroxide antioxidant is 4-hydroxy-2,2,6,6-tetramethylpiperidine-1-oxyl. In some embodiments, the eukaryotic cell is a cancer cell. In some embodiments, the expression level of the one or more genes is decreased in a tissue selected from the group consisting of a skin tissue, an immune tissue, an adipose tissue, a pancreatic tissue, cardiac tissue, and a neuronal tissue. In some embodiments, the expression level of the one or more genes is age-related. In some embodiments, the expression level of the one or more genes is disease-related. In some embodiments, the expression level of the one or more genes is neurodegenerative-related.

Some embodiments disclosed herein provide methods for treating a condition comprising identifying an individual known to have a condition mediated by xenobiotic toxicity administering to the individual an effective amount of a nitroxide antioxidant, whereby an expression level of a glutathione S-transferase is increased. In some embodiments, the gene is selected from the group consisting of Gstm3, Gstm6, Gsta3, Gstt1, Gsta4, Gstm1, Gstm4, Gstt2, Gstp1, and Gstk1. In some embodiments, the nitroxide antioxidant is 4-hydroxy-2,2,6,6-tetramethylpiperidine-1-oxyl. In some embodiments, the condition is age-related. In some embodiments, the condition is cancer. In some embodiments, the condition is a disease. In some embodiments, the condition is a neurodegenerative disorder. In some embodiments, the condition is an infection. In some embodiments, the condition is associated with an oxidative stress. In some embodiments, the condition is chemotherapy-induced toxicity. In some embodiments, the condition is radiation-induced toxicity. In some embodiments, the xenobiotic toxicity is caused by oxidative stress.

Some embodiments disclosed herein provide methods for ameliorating xenobiotic induced oxidative stress comprising administering an effective amount of a nitroxide antioxidant to an individual known to have xenobiotic induced oxidative stress whereby an expression level of one or more GST genes is upregulated. In some embodiments, the gene is selected from the group consisting of Gstm3, Gstm6, Gsta3, Gstt1, Gsta4, Gstm1, Gstm4, Gstt2, Gstp1, and Gstk1. In some embodiments, the nitroxide antioxidant is 4-hydroxy-2,2,6,6-tetramethylpiperidine-1-oxyl. In some embodiments, the xenobiotic induced oxidative stress is age-related. In some embodiments, the xenobiotic induced oxidative stress is related to cancer. In some embodiments, the xenobiotic induced oxidative stress is related a disease. In some embodiments, the xenobiotic induced oxidative stress is related to neurodegenerative disorder. In some embodiments, the xenobiotic induced oxidative stress is related to an infection. In some embodiments, the xenobiotic induced oxidative stress is related to one or more exogenous factors. In some embodiments, the xenobiotic induced oxidative stress is related to one or more endogenous factors. In some embodiments, the individual has been administered a chemotherapeutic agent. In some embodiments, the nitroxide antioxidant is chemically attached to one or more bioeffector molecules.

Some embodiments disclosed herein provide methods for preventing a condition comprising identifying an individual at risk of xenobiotic toxicity administering to the individual an effective amount of a nitroxide antioxidant, whereby an expression level of a glutathione S-transferase is increased. In some embodiments, the gene is selected from the group consisting of Gstm3, Gstm6, Gsta3, Gstt1, Gsta4, Gstm1, Gstm4, Gstt2, Gstp1, and Gstk1. In some embodiments, the nitroxide antioxidant is 4-hydroxy-2,2,6,6-tetramethylpiperidine-1-oxyl. In some embodiments, the condition is age-related. In some embodiments, the condition is cancer. In some embodiments, the condition is a disease. In some embodiments, the condition is a neurodegenerative disorder. In some embodiments, the condition is an infection. In some embodiments, the condition is associated with an oxidative stress. In some embodiments, the xenobiotic toxicity is chemotherapy-induced. In some embodiments, the xenobiotic toxicity is radiation-induced. In some embodiments, the xenobiotic toxicity is caused by oxidative stress. In some embodiments, the individual has been administered or exposed to a xenobiotic, wherein the effective amount of a nitroxide antioxidant is administered prior to the administration or exposure to the xenobiotic. In some embodiments, the individual has been administered or exposed to a xenobiotic, wherein the effective amount of a nitroxide antioxidant is administered in conjunction with the administration or exposure to the xenobiotic. In some embodiments, the method further comprises administering or exposing to the individual a xenobiotic prior to administering to the individual the effective amount of the nitroxide antioxidant. In some embodiments, administering to the individual the effective amount of a nitroxide antioxidant comprises administering or exposing to the individual a xenobiotic.

DETAILED DESCRIPTION

Definitions

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, N.Y. 1994); Sambrook et al., Molecular Cloning, A Laboratory Manual, Cold Springs Harbor Press (Cold Springs Harbor, N.Y. 1989). For purposes of the present disclosure, the following terms are defined below.

All patents, applications, published applications and other publications referred to herein are incorporated by reference for the referenced material and in their entireties. If a term or phrase is used herein in a way that is contrary to or otherwise inconsistent with a definition set forth in the patents, applications, published applications and other publications that are herein incorporated by reference, the use herein prevails over the definition that is incorporated herein by reference.

As used herein, the term "expression" means that a gene product is expressed or produced by one or more nucleic acid molecules at a level detectable by standard molecular biology methods, which gene product refers to e.g. an unspliced RNA, an mRNA, a splice variant mRNA, a polypeptide, a post-translationally modified polypeptide, a splice variant polypeptide etc., and specifically products made using an RNA gene product as a template, e.g. cDNA of the RNA.

As used herein, "differential expression" of a gene means that the expression of the gene is at a higher level ("increased expression") or lower level ("decreased expression") in a human subject suffering from a disease, for example cancers and autoimmune diseases, relative to its expression in a normal or control subject. Differential expression includes both quantitative, as well as qualitative, differences in the temporal or cellular expression pattern in a gene or its expression products among, for example, normal and diseased cells, or among cells which have undergone different disease events or disease stages.

As used herein, "increasing the expression level" of a gene means causing the expression of the gene to increase by treating the human subject with a compound, for example a nitroxide antioxidant, such that the expression level of the gene after treatment is higher than the expression level of the gene before treatment in the human subject.

It is understood that aspects and embodiments of the invention described herein include "consisting" and/or "consisting essentially of" aspects and embodiments.

Other objects, advantages and features of the present invention will become apparent from the following specification taken in conjunction with the accompanying drawings.

Human Subject Identification

The present disclosure relates to methods of treating alteration in gene expression. It has been shown that the expression level of a number of genes, such as ones playing important roles in cell detoxification and regulation is decreased in aging human beings, human subjects with certain diseases (e.g., age-related diseases, such as Alzheimer), and/or human subjects susceptible to certain diseases. Gene expression changes also play important roles in aging and serve as biomarkers of physiological decline and disease conditions, such as Alzheimer's disease. Decreased gene expression levels, due to accumulation of DNA damages, have been observed in the human brain (Lu et al. Nature (2004) 429, 883-891; the content of which is hereby incorporated by reference in its entirety).

Disclosed herein are methods of treating a human subject having a decrease or downregulation in gene expression levels (e.g., a decrease in gene expression levels), such as those genes associated with glutathione S-transferase (GST)

or GST activity. In some embodiments, the human subject can be identified based on the human subject's age, gene expression level, family history, health conditions, medical history, habits, or a combination thereof.

In some embodiments, the human subject may have an age that is, is about, or is over 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 years old.

In some embodiments, the human subject is identified based on the human subject's expression profiles of one or more genes associated with glutathione S-transferase. Non-limiting exemplary methods for determining the human subject's expression profiles include: amplification techniques such as PCR and RT-PCR (including quantitative variants), hybridization techniques such as in situ hybridization, microarrays, blots, and others, and high throughput sequencing techniques like Next Generation Sequencing (Illumina, Roche Sequencer, Life Technologies SOLID™), Single Molecule Real Time Sequencing (Pacific Biosciences), True Single Molecule Sequencing (Helicos), or sequencing methods using no light emitting technologies but other physical methods to detect the sequencing reaction or the sequencing product, like Ion Torrent (Life Technologies). Non-limiting exemplary methods for determining the human subject's expression profiles include: binding techniques such as ELISA, immunohistochemistry, microarray and functional techniques such as enzymatic assays.

Glutathione Activity and Glutathione S-Transferase Activity

In some embodiments, administering to a human subject, having or known to have a decreased glutathione activity, an effective amount of a nixtroxide antioxidant can result in increased expression level of at least one gene encoding a glutathione S-transferase (GST) enzyme and/or increased glutathione activity. The expression level of the at least one gene encoding the GST enzyme and/or the glutathione activity in the human subject (e.g., in one or more cells, cell types, tissues, or organs) can increase after administering the human subject with the effective amount of the nitroxide antioxidant. The decrease in expression levels of genes associated with GST or GST activity can result in decreased glutathione activity (e.g., in one or more cells, cell types, tissues, or organs). In some embodiments, decreased expression levels of the genes associated with GST can result in decreased concentration of one or more proteins associated with GST (e.g., Gstm3, Gstm6, Gsta3, Gstt1, Gsta4, Gstm1, Gstm4, Gstt2, Gstp1, and Gstk1). These proteins can conjugate xenobiotics with glutathione. Thus, decreased expression of the genes associated with GST activity may result in decreased glutathione activity.

Regardless of the cause of the decrease or downregulation, some common terminology can be used. In some embodiments, the expression level of a gene (e.g., a gene associated with GST) or glutathione activity in a human subject is considered to be downregulated or decreased if the decrease in the expression level of that gene or glutathione activity is statistically significant compared to that of a control or a reference. The control or reference can be, for example, a normal healthy population, a population at large, a collection of individuals of the same age or condition or sex, or the same human subject at a different time (e.g., at an earlier time of life when the human subject does not have the disease or condition that results in the downregulation).

In some embodiments, a normal healthy population or a population at large can be a population having the same or similar gender, age, and/or race, compared to the human subject. In some embodiments, the expression level of the gene in the control or reference can be the mean or median expression level of the gene in control subjects in the control or reference subjects in the reference. The decrease in expression level or glutathione activity can be statistically significant if the probability of the observed difference occurring not by chance, the confidence level, is greater than a threshold. The threshold can be, or be about, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.9%, or a number or a range between any two of these values.

In some embodiments, the decrease in expression level or decrease in glutathione activity can be, or be about, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 20%, 30%, 40%, 50%, 60%, 70%, 80%, 90%, 100%, or a number or a range between any two of these values. In some embodiments, the decrease in expression level can be at least 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 20%, 30%, 40%, 50%, 60%, 70%, 80%, 90%, 100%, or more.

In some embodiments, the expression level of the at least one gene encoding the glutathione S-transferase enzyme and/or the glutathione activity in the human subject is increased following administering the human subject with the effective amount of the nitroxide antioxidant. The expression level of the at least one gene encoding the GST enzyme or glutathione activity in the human subject is considered to have increased if the increase in the expression level of that gene or glutathione activity is statistically significant compared to that of a control or a reference. The control or reference can be, for example, the same human subject at a different time (e.g., before the nitroxide antioxidant is administered). As another example, the control or reference can include, or based on, individuals of the same age, condition (e.g., individuals having a decreased expression level of the at least one gene encoding the GST enzyme, or having decreased glutathione activity, without being administered the nitroxide antioxidant, such as being administered a placebo), and/or sex.

In some embodiments, the increase in expression level or increase in glutathione activity can be, or be about, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 20%, 30%, 40%, 50%, 60%, 70%, 80%, 90%, 100%, or a number or a range between any two of these values. In some embodiments, the increase in expression level can be at least 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 20%, 30%, 40%, 50%, 60%, 70%, 80%, 90%, 100%, or more.

Genes Associated with the Glutathione S-Transferase

In some embodiments, administering to the human subject the effective amount of the nitroxide antioxidant results in an increased expression level of a gene, for example a gene associated with glutathione S-transferase. Some embodiments disclosed herein provide methods for treating an individual in need thereof, comprising identifying an individual having a disease-related decreased expression level of a gene associated with glutathione S-transferase (GST); and administering to the individual an effective amount of a nitroxide antioxidant to increase the level of expression of the gene associated with glutathione S-transferase. Some embodiments disclosed herein provide methods for treating an individual in need thereof, comprising identifying an individual in need of an increased expression level of a gene associated with glutathione S-transferase; and administering to the individual an effective amount of a nitroxide antioxidant to increase the level of expression of the gene associated with glutathione S-transferase.

Non-limiting examples of diseases associated with and altered level of glutathione S-transferase (e.g., decreased expression level of GST) include cancer; breast cancer; lung cancer; kidney cancer; cancers of the ovary and uterus; cancer of the central nervous system; cancers of the head and neck; melanoma; lymphomas; leukemia; neurological disorders; Alzheimer's disease; Parkinson's disease; Huntington's disease; amyotrophic lateral sclerosis; stroke; cardiovascular disorders; ischemia; heart failure; infectious diseases; bacterial infections; viral infections; autoimmune diseases; systemic lupus erythematosus; autoimmune lymphoproliferative syndrome; rheumatoid arthritis; and thyroiditis.

Non-limiting exemplary genes associated with glutathione S-transferase (e.g., genes involved in glutathione S-transferase activity) include those in the glutathione S-transferase family (Gsta1, Gsta2, Gsta3, Gsta4, Gsta5, Gsta6P, Gsta7P, Gstk1, Gstm1, Gstm2, Gstm3, Gstm4, Gstm5, Gsto1, Gsto2, Gsto3P, Gstp1, Hpgds, Gstt1, Gstt2, Gstt2B, Gstz1).

The gene associated with glutathione S-transferase can be Gstm3, Gstm6, Gsta3, Gstt1, Gsta4, Gstm1, Gstm4, Gstt2, Gstp1, or Gstk1. For example, the treatment (e.g., administering to a human subject a nitroxide antioxidant) can result in increased expression levels of Gstm3, Gstm6, Gsta3, Gstt1, Gsta4, Gstm1, Gstm4, Gstt2, Gstp1, Gstk1, or any combination thereof. The increased expression levels of Gstm3, Gstm6, Gsta3, Gstt1, Gsta4, Gstm1, Gstm4, Gstt2, Gstp1, Gstk1, or any combination thereof, can increase glutathione (GSH) level or activity (e.g., the activity of the reduced form of GSH as a reducing agent, or the GSH reducing activity). The increased level of GSH activity can result in a diminished cellular toxicity and thereby a decrease in or disappearance of signs and symptoms of a disease associated with decreased glutathione S-transferase expression, such as the curing of the disease associated with decreased glutathione S-transferase expression.

Glutathione S-Transferase

Glutathione S-transferase (GST) can describe a gene family having numerous genes in multiple subfamilies. In a particular embodiment, the GST family of genes includes multiple genes in multiple subfamilies, such as alpha (Gsta), mu (Gstm), omega (Gsto), pi (Gstp), theta (Gstt) and zeta (Gstz) (Nebert et al. Analysis of the glutathione S-transferase (GST) gene family. *Human Genomics* (2004) 1(6): 460-464. doi.org/10.1186/1479-7364-1-6-460; the content of which is hereby incorporated by reference in its entirety). Members of the glutathione S-transferase gene family encode genes that are critical for certain biological processes, as well as for detoxication and toxification mechanisms, via conjugation of reduced glutathione (GSH) with numerous substrates such as pharmaceuticals and environmental pollutants. The GST genes are upregulated in response to oxidative stress.

Human GSTs can be classified into three main families: cytosolic, mitochondrial (e.g., GST class kappa, including GSTK1) and membrane-bound microsomal. Microsomal GSTs, such as MGST1, MGST2, and MGST3, are designated as "membrane-associated proteins in eicosanoid and glutathione metabolism" (MAPEGs). MAPEGs are structurally distinct from cytosolic GSTs but are functionally similar in the ability to catalyse the conjugation of GSH to electrophilic compounds (Hayes et al. Glutathione Transferases. Annual Review of Pharmacology and Toxicology (2005) 45(1):51-88; the content of which is incorporated herein by reference in its entirety).

The mammalian cytosolic family of GSTs exist as monomers and are catalytically active in a homo- or heterodimeric state. The cytosolic family is further divided into multiple classes: alpha, mu, omega, pi, sigma, theta and zeta. Classification is based on sharing greater than 60% identity within a class and focuses mainly on the more highly conserved N-terminal domain that contains a catalytically active tyrosine, cysteine or serine residue. The catalytic residue, also referred to as G-site, interacts with the thiol group of GSH. A substrate binding site (H-site) facilitates catalysis and is in proximity to the G-site (McIlwain. Glutathione S-transferase polymorphisms: cancer incidence and therapy. *Oncogene* (2006) 25:1639-1648. doi:10.1038/sj.onc.1209373; the content of which is incorporated herein in its entirety).

The alpha subfamily includes Gsta1, Gsta2, Gsta3, Gsta4, and Gsta5. The kappa subfamily includes Gstk1. The mu subfamily includes Gstm1, Gstm1L (RNAi), Gstm2, Gstm3, Gstm4, and Gstm5. The omega subfamily includes Gsto1 and Gsto2. The pi family includes Gstp1. The theta subfamily includes Gstt1, Gstt2, and Gstt4. The zeta subfamily includes Gstz1 (also known as Gstz1 MAAI-Maleylacetoacetate isomerase). The microsomal subfamily includes mGst1, mGst2, and mGst3.

An example of GST catalytic activities is the capacity of these enzymes to lower the $pK_a$ of the sulfhydryl group of reduced GSH from 9.0 in aqueous solution to about 6.5 when GSH is bound in the active site (Armstrong. Glutathione S-transferases: structure and mechanism of an archetypical detoxication enzyme. Adv. Enzymol. Relat. Areas. Mol. Biol. (1994) 69:1-44; the content of which is incorporated herein in its entirety). GSH exists as the thiolate (GS) anion at neutral pH when complexed with the GST enzyme. Catalysis by GST occurs through the combined capacity of the enzyme to promote $GS^-$ formation and to bind hydrophobic electrophilic compounds at a closely adjacent site (Hayes J D, Pulford D. Crit Rev Biochem Mol Biol. 1995. The glutathione S-transferase supergene family: regulation of GST and the contribution of the isoenzymes to cancer chemoprotection and drug resistance. 30(6):445-600; the disclosure of which is incorporated herein in its entirety). GST has been identified to have multiple substrate binding sites and each site may support specific affinity for particular categories and classes of xenobiotic substrates.

Other non-limiting examples of GST activity are detoxifying electrophilic xenobiotics, such as chemical carcinogens, environmental pollutants, and antitumor agents. For example, these transferases can inactivate endogenous alpha,beta-unsaturated aldehydes, quinones, epoxides, and hydroperoxides formed as secondary metabolites during oxidative stress. GST enzymes are also intimately involved in the biosynthesis of leukotrienes, prostaglandins, testosterone, and progesterone, as well as the degradation of tyrosine (Hayes et al. Glutathione Transferases. Annual Review of Pharmacology and Toxicology (2005) 45:51-88; the content of which is incorporated herein in its entirety).

Numerous polymorphisms exist in the human GST genes (Coles B F, Kadlubar FF Biofactors. Detoxification of electrophilic compounds by glutathione S-transferase catalysis: determinants of individual response to chemical carcinogens and chemotherapeutic drugs? (2003) 17(1-4):115-30; the content of which is incorporated herein in its entirety). For example, particular polymorphisms may result in the complete absence of the Gstm1 or the Gstt1 gene. Given such absence in certain GST activities leads to decreased detoxification of environmental carcinogens or chemotherapeutic agents and thus to clinical problems in patients lacking these genes.

Polymorphisms are generally defined by one or more mutations in the DNA sequence for the GST genes. Genotypical polymorphisms in the GST genes often manifest in a decreased expression of the gene or null phenotypes. Decreased expression of GST genes directly inhibits enzymatic activity and conjugation of GSH with the various substrates. Such decreased activity increases risk associated with diseases and conditions. Null expression, where enzyme activity is severely diminished or non-existent, is often used as a biomarker for disease and condition susceptibility.

In some embodiments, polymorphic genotypical decreased or non-existent GST enzymatic activity within one or more of the particular GST genes results in increased incidence, occurrence, susceptibility, or risk of developing, promoting, contracting, or inheriting certain disease or conditions. In some embodiments, administering to a human subject in need thereof a nitroxide antioxidant can decreased incidence, occurrence, susceptibility, or risk of developing, promoting, contracting, or inheriting certain disease or conditions (e.g., due to polymorphic genotypical decreased or non-existent GST enzymatic activity within one or more of the particular GST genes). In other embodiment, combined polymorphisms within the GST gene family results in increased incidence, occurrence, susceptibility, or risk of developing, promoting, contracting, or inheriting certain disease or conditions.

In an embodiment, GSTs are detoxification enzymes that can counter ageing-associated oxidative and chemical stresses. The transcript of a distinct subclass of human GSTs (hGstm3) has been shown by RNA blot analysis to be widely distributed in different regions of adult brain.

Further, interaction with regulator molecules such as nuclear factor erythroid 2-related factor 2 (NRF2) supports the roles of GSH and GST in antioxidant pathways. NRF2 has been shown to control several different antioxidants pathways. The first is glutathione (GSH) production and regeneration, which is regulated by the following antioxidants: the glutamate-cysteine ligase complex modifier subunit (GCLM), the GCL catalytic subunit (GCLC), the cystine/glutamate transporter XCT and glutathione reductase (GSR). The second is GSH utilization, which is regulated by the glutathione S-transferases (Gsta1, Gsta2, Gsta3, Gsta5, Gstm1, Gstm2, Gstm3 and Gstp1) and glutathione peroxidase 2 (GPX2) (Chiara Gorrini, et al., Modulation of oxidative stress as an anticancer strategy. Nature Reviews Drug Discovery (2013) 12:931-947. doi:10.1038/nrd4002; the disclosure of which is incorporated herein in its entirety).

Treating a subject with a nitroxide antioxidant may promote desirable increase in expression levels of one or more GST genes in a particular subset population affected or defined by symptoms or physical manifestation of a disease or condition (e.g., a disease or condition associated with oxidative stress). Oxidative stress is the imbalance between oxidant-antioxidant systems and may play a major role in the psoriasis pathogenesis. Cytochrome (CYP) is a family of enzymes that are responsible for the metabolism of various endogenous and exogenous substances such as drug metabolism. In some embodiments, the antioxidant system is the glutathione S-transferases (GST), which decrease oxidative stress by reducing oxidative products (Akbulak et al. Evaluation of oxidative stress via protein expression of glutathione S-transferase and cytochrome p450 (CYP450) isoenzymes in psoriasis vulgaris patients treated with methotrexate. Cutan Ocul Toxicol. (2017) 3:1-6. doi: 10.1080/15569527.2017.1369431; the content of which is incorporated herein in its entirety).

Gstm1

Glutathione S-transferase mu 1 (Gstm1) is a gene encoding an enzyme within the mu class of GST enzymes. Functions of Gstm1 includes the detoxification of electrophilic compounds, such as carcinogens, therapeutic drugs, environmental toxins and products of oxidative stress, by conjugation with glutathione. The genes encoding the mu class of enzymes are highly polymorphic.

Inheritance of the combined Gstm1 and Gstt1 null genotypes showed a significant increase in risk (crude odds ratio (OR)=2.32, 95% confidence interval (CI)=1.01-6.04). Based on adjustment by age, gender and smoking history, the myeloperoxidase (MPO) 463G>A (GA) polymorphisms has been shown to interact with the presence of Gstm1 and Gstt1 genotypes to significantly reduce the risk (OR=0.17, 95% CI=0.03-0.98). From the chromosome aberration (CA) study in a subgroup of 79 patients and 69 matched controls, patients had significantly more CA than the controls. Among the patients, Gstm1 null was associated with a significant increase of CA and MPO AA was associated with a significant decrease of CA compared to their respective wild-type genotypes (Cajas-Salazar et al. Combined effect of MPO, GSTM1 and GSTT1 polymorphisms on chromosome aberrations and lung cancer risk. *International journal of hygiene and environmental health* (2003); the content of which is incorporated herein in its entirety).

Gstm1 homozygotes (51.1%) have been registered in Cystic Fibrosis (CF) patients of the pancreatic sufficient group with clear-cut pulmonological manifestations but not in those of the pancreatic insufficient group with predominantly intestinal or mixed clinical symptoms (41.2% and 37.5%, respectively). Earlier clinical manifestations and death before the age of 5 years are typical for Gstm1-deleted CF patients. These data support the use of Gstm1 deletion as a convenient genetic marker for the early detection of groups at higher risk of many diseases caused by environmental and genetic factors, where manifestation depends on the lack of detoxification (Baranov et al., Proportion of the Gstm1 0/0 genotype in some Slavic populations and its correlation with cystic fibrosis and some multifactorial diseases. *Hum. Genet*. (1996); the content of which is incorporated herein in its entirety).

A common genetic polymorphism divides the population of never smokers into two groups of approximately equal size, one (homozygous carriers of the Gstm1 null allele) that has a statistically significant greater risk of lung cancer from ETS than the other (heterozygous or homozygous carriers of the wild-type Gstm1 allele) (Bennett et al. Environmental tobacco smoke, genetic susceptibility, and risk of lung cancer in never-smoking women. *Natl. Cancer Inst*. (1999); the content of which is incorporated herein in its entirety).

The Gstm1 homozygous null genotype was associated with an increased risk of developing breast cancer (OR=2.10; 95% CI=1.22-3.64), principally due to an association with postmenopausal breast cancer (OR=2.50; 95% CI=1.34-4.65). For Gstp1, experimental data suggest a trend of increasing risk with higher numbers of codon 105 valine alleles (compared with isoleucine alleles); a 1.97-fold increased risk of breast cancer (95% CI=0.77-5.02) was associated with valine/valine homozygosity. The risk of breast cancer associated with the Gstt1 homozygous null genotype was 1.50 (95% CI=0.76-2.95). The risk of breast cancer increased as the number of putative high-risk genotypes increased (P for trend <0.001) (OR=3.77; 95% CI=1.10-12.88 for a combined genotype of Gstm1 null, Gstt1 null, and either Gstp1 valine heterozygosity or Gstp1 valine homozygosity) (Helzlsouer et al. Association between glutathione S-transferase M1, P1, and T1 genetic polymorphisms and development of breast cancer. *Natl. Cancer Inst.* (1998); the content of which is incorporated herein in its entirety).

Individuals who lacked the Gstm1 gene and possessed a NAT2 slow-acetylator genotype had a higher risk of developing malignant and nonmalignant pulmonary disorders that was approximately fivefold greater than that observed for those who had the Gstm1 gene and a NAT2 fast-acetylator genotype (OR=5.1; 95% CI=1.6-17.6). These individuals had a fourfold increased risk of developing nonmalignant pulmonary disorders (OR=4.1; 95% CI=1.1-17.2) and an eightfold increased risk of developing malignant mesothelioma (OR=7.8; 95% CI=1.4-78.7) when compared with the same reference group (Hirvonen et al. Glutathione S-transferase and N-acetyltransferase genotypes and asbestos-associated pulmonary disorders. *Natl. Cancer Inst.* (1996); the content of which is incorporated herein in its entirety).

Certain GST enzymes have been implicated in the formation and scavenging of the ultimate reactive metabolites, the diolepoxides, from polycyclic aromatic hydrocarbons (PAHs). In a study on aluminum smelter workers, airborne polycyclic aromatic hydrocarbons (PAH), the pyrene metabolite 1-hydroxypyrene (1-OHP) in urine, and genotypes for biotransformation enzymes involved in PAH metabolism were analyzed to evaluate the correlation between external exposure and biomarkers of exposure and to investigate to what extent genetic polymorphism in metabolic enzymes can explain inter-individual variation in urinary 1-OHP levels. Eight polymorphisms in the Cytochrome P450 Family 1 Subfamily A Member 1 (CYP1A1), microsomal epoxide hydrolase (mEH), Gstm1, Gstp1 and Gstt1 genes were analyzed. The 1-OHP excretion was found to correlate significantly (P$\leq$0.005) to the exposure. Polymorphisms were a specific factor identified as an explanation for the variations. In particular, polymorphisms in the cytochrome P450 1A1, Gstm1 and Gstt1 enzymes. Ultimately, the polymorphisms coincided with the magnitude of variation (Alexandrie et al. CYP1A1 and GSTM1 polymorphisms affect urinary 1-hydroxypyrene levels after PAH exposure. Alexandrie. *Carcinogenesis* (2000); the content of which is incorporated herein in its entirety).

Oxidative stress is known to be implicated in the pathogenesis of hyper tension, among other conditions. Decreased GST gene expression in conjunction with oxidative stress allow for identification of individuals at risk or otherwise predisposed to certain conditions. A specific example provides for, GST Gstm1 and Gstt1 null genotypes may serve as predisposing factors for essential hypertension (Eslami S. & Sahebkar A. Glutathione-S-transferase M1 and T1 null genotypes are associated with hypertension risk: a systematic review and meta-analysis of 12 studies. Curr Hypertens Rep. (2014) 16, 432, doi:10.1007/s11906-014-0432-1; the content of which is incorporated herein by reference in its entirety).

Gstm3

Glutathione S-transferase mu 3 (Gstm3) is a gene encoding an enzyme Gstm3. Gstm3 is a member of the mu sub family of GST genes, which are involved in the detoxification of electrophilic compounds, including some carcinogens, therapeutic drugs, environmental toxins and products of oxidative stress, by conjugation with glutathione.

Genetic variations of Gstm3, such as polymorphisms have been shown to result in decreased expression of Gstm3. It has been shown genetic variations can change an individual's susceptibility to carcinogens and toxins as well as affect the toxicity and efficacy of certain drugs. Gstm3 is also implicated in the prognosis of childhood Acute Lymphocytic Leukemia (Kearns et al. Mu class glutathione S-transferase mRNA isoform expression in acute lymphoblastic leukaemia. *Haematol.* (2003); the content of which is incorporated herein in its entirety). Genetic variants can result in decreased functional activity of the encoded GST enzyme. Increased expression of a wild-type or genetic variant can increase, for example, by administering to a human subject a nitroxide antioxidant, enzyme concentration and thereby associated activity of the encoded enzymes.

HPLC profiles have indicated that the human Gstm3 (hGstm3) subunit was the second most abundant GST subunit in brain. Immunocytochemistry performed with hGstm3-specific antisera, showed prominent staining of neuritic plaques, neurofibrillary tangles and microglia in sections of hippocampus obtained from patients with Alzheimer's disease. (Tatyana Tchaikovskaya et al., Glutathione S-transferase hGstm3 and ageing-associated neurodegeneration: relationship to Alzheimer's disease, In Mechanisms of Ageing and Development (2005) 126(2): 309-315. doi.org/10.1016/j.mad.2004.08.029; the disclosure of which is incorporated herein in its entirety). Therefore, Gstm3 presence in the brain can inhibit progression of neurodegenerative diseases mediated by xeniobiotic compounds, such as plaques through their conjugation with GSH.

Gstm3, as well as Gstm2, may play crucial roles in temperature regulation, nociception, and sleep-wake regulation by producing PGE2 in the brain (Beuckmann et al. Identification of mu-class glutathione transferases M2-2 and M3-3 as cytosolic prostaglandin E synthases in the human brain. *Neurochem. Res.* (2000); the disclosure of which is incorporated herein in its entirety). Therefore, where an individual is found to have decreased Gstm3 and/or Gstm2, homeostatic functions are dysregulated. Increasing expression of Gstm3 and/or Gstm2 can increase their respective biological functions, including proper regulation of such functions as temperature regulation, nociception, and sleep-wake regulation.

Gstm4

Glutathione S-transferase mu 4 (Gstm4) is one of the four isoenzymes identified for the mu class of GST enzymes. The gene, located on chromosome 1, is comprised of eight exons with an organization similar to that of other Mu class genes (Taylor et al. Gstm4 differs from a partial gene sequence, termed GSTmu2. Biochem. J. (1991) 274, 587-593; the content of which is incorporated herein in its entirety).

Polymorphisms in GST genotype result in loss or decreased activity of the GST gene family. Although a polymorphism may result in loss of function, the adaptive compensation regarding GST activity relating to the lost function of one GST gene may be compensated for by other genes in the GST family. Therefore, although one or more GST genes may be a null phenotype resulting in loss of function, increased expression of one or more other GST genes can compensate for the loss GST function. For example, loss of Gstm4 expression is a frequent event in the development of non-small cell lung cancer (NSCLC). Promoter hypermethylation of Gstm4 does not account for this loss of expression. Other intrinsic or extrinsic factors may contribute to the transcriptional silencing of Gstm4 in the molecular pathogenesis of NSCLC (Xinarianos et al. Analysis of GSTM4 in non-small cell lung cancer. Cancer Res. (2007); the content of which is incorporated herein in its entirety).

Gstm6

Glutathione S-transferase mu 6 (Gstm6) is active in the conjugation of reduced glutathione to a wide number of exogenous and endogenous hydrophobic electrophiles. Part of the mu sub family of GST genes, the enzymatic activity of Gstm6 includes supporting cellular detoxification and GSH facilitated removal of xenobiotics and proinflammatory factors.

Gstm6 is expressed in multiple tissues, including the small intestine. Oxidative stress and lipid peroxidation have been shown to contribute to the pathogenesis of intestinal ischemic diseases (Thomson et al., Oxidative stress and antioxidants in intestinal disease. Dig Dis. (1998) 16(3):152-8; the content of which is incorporated herein in its entirety). Increased Gstm6 expression in the small intestine serves to facilitate increased neutralization of free radicals. Mucosal integrity is maintained by the luminal redox status of the glutathione/glutathione disulfide (GSH/GSSG) and cysteine/cystine (Cys/CySS) couples which also support luminal nutrient absorption, mucus fluidity, and a diverse microbiota. Glutathione disulfide (GSSG) is a disulfide derived from two glutathione molecules. The epithelial layer is uniquely organized for rapid self-renewal that is achieved by the well-regulated processes of crypt stem cell proliferation and crypt-to-villus cell differentiation. The GSH/GSSG and Cys/CySS redox couples, known to modulate intestinal cell transition through proliferation, differentiation or apoptosis, could govern the regenerative potential of the mucosa (Circu et al. Intestinal redox biology and oxidative stress. *Seminars in Cell & Developmental Biology*, (2012) 23(7):729-737. doi.org/10.1016/j.semcdb.2012.03.014; the disclosure of which is incorporated herein in its entirety). Therefore, the increased expression of Gstm6 (e.g., by administering a nitroxide antioxidant to a human subject in need thereof) can support GSH activity or function and conjugation of xenobiotic substrates from oxidative stress to detoxify cells within the small intestine.

Therapies used to treat conditions such as cancer can produce negative side effects resulting in oxidative stress. For example, methotrexate is a common treatment for many types of cancer and is well known to result in increased oxidative stress. Treatment of rats with methotrexate have been shown to induce the oxidative stress in the small intestine. The reactive oxygen species (ROS) production has been observed to precede an increase of myeloperoxidase activity, which suggested neutrophil infiltration. The increased ROS production can result in damage to the small intestine. Increased expression of Gstm6, and specifically increases in the small intestine may be effective to prevent and treat methotrexate-induced small intestine damage (Miyazono. Oxidative stress contributes to methotrexate-induced small intestinal toxicity in rats. Scand J Gastroenterol. (2004) 39(11):1119-27; the content of which is incorporated herein in its entirety).

Gsta3

Glutathione S-transferase alpha 3 (Gsta3) gene encodes a glutathione S-tranferase belonging to the alpha class genes that are located in a cluster mapped to chromosome 6. Genes of the alpha class are highly related and encode enzymes with glutathione peroxidase activity. However, during evolution, this alpha class gene diverged accumulating mutations in the active site that resulted in differences in substrate specificity and catalytic activity. The enzyme encoded by Gsta3 catalyzes the double bond isomerization of precursors for progesterone and testosterone during the biosynthesis of steroid hormones.

Gsta3 has been found to efficiently catalyze obligatory double-bond isomerizations of $\Delta^5$-androstene-3,17-dione and $\Delta^5$-pregnene-3,20-dione, precursors to testosterone and progesterone, respectively, in steroid hormone biosynthesis. The catalytic efficiency ($k_{cat}$/K m) with $\Delta^5$-androstene-3,17-dione was determined as $5\times10^6$ $M^{-1}$ $s^{-1}$, which is considerably higher than with any other GST substrate tested. The rate of acceleration afforded by Gsta3 is $6\times10^8$ based on the ratio between $k_{cat}$ and the rate constant for the nonenzymatic isomerization of $\Delta^5$-androstene-3,17-dione. Besides being high in absolute numbers, the $k_{cat}$/K m value of Gsta3 exceeds by a factor of ~230 that of 3β-hydroxysteroid dehydrogenase/isomerase, the enzyme generally considered to catalyze the $\Delta^5$-$\Delta^4$ double-bond isomerization. Furthermore, Gsta3-specific polymerase chain reaction analysis of cDNA libraries from various tissues showed a message only in those characterized by active steroid hormone biosynthesis, indicating a selective expression of Gsta3 in these tissues (Johansson et al. Human Glutathione Transferase A3-3, a Highly Efficient Catalyst of Double-bond Isomerization in the Biosynthetic Pathway of Steroid Hormones. The Journal of Biological Chemistry (2001) 276:33061-33065; the content of which is incorporated herein in its entirety).

The soluble GSTs occur as an enzyme superfamily of dimeric proteins playing a prominent role in the inactivation of numerous toxic electrophiles of both exogenous and endogenous origins, such as xenobiotic compounds. The majority of these detoxication reactions involve conjugation of GSH with the toxin via nucleophilic attack on the electrophilic center in the second substrate. The GSTs are grouped into different classes primarily based on primary structure. Variations of the amino acid residues that make up the electrophilic substrate-binding site (H-site) in different isoenzymes provide the GST family with the ability to catalyze reactions toward a large number of structurally diverse substrates. For example, in the Alpha class Gsta4 exhibits high catalytic efficiency with biologically relevant alkenal substrates, whereas Gsta1 and Gsta2 efficiently catalyze the reduction of fatty acid and phospholipid hydroperoxides. The isomerization of endogenous steroids differs from the ordinary type of GST-catalyzed reaction, because the GSH molecule serves as a base in the mechanism and is not consumed in the process. (Ann-Sofie Johansson (2001)).

Gsta4

Glutathione S-transferase alpha 4 (Gsta4) is an alpha-class member of the GST gene family. Primary functions include conjugation of reduced glutathione to a wide number of exogenous and endogenous hydrophobic electrophiles. This enzyme has a high catalytic efficiency with 4-hydroxyalkenals, such as 4-hydroxynonenal (4-HNE). Human glutathione transferase A4 crystal structures and mutagenesis have revealed the basis of high catalytic efficiency with toxic lipid peroxidation products (Bruns et al. J. Mol. Biol. (1999) 288:427-439; the content of which is incorporated herein in its entirety).

The metabolism of 4-HNE is, although not entirely, conjugative, and proceeds via Michael addition of glutathione to the double bond of 4-HNE. This reaction is catalyzed by specialized glutathione S-transferases (GSTs) exemplified by Gsta4. Mice homozygous for the disrupted mGsta4 allele were viable and appeared normal except for lower litter size, higher fat content in bones, and greater susceptibility to bacterial infection. The null mice had a significantly lower survival time than wild-type controls when chronically treated with relatively low doses of paraquat, a finding consistent with a role of Gsta4 in the defense against oxidative stress. (Engle et al., Physiological role of mGSTA4-4, a glutathione S-transferase metabolizing 4-hydroxynonenal: generation and analysis of mGsta4 null mouse, Toxicology and Applied Pharmacology (2004) 194 (3):296-308; the content of which is incorporated herein in its entirety).

Gsta4 is one of the enzymes responsible for the removal of 4-hydroxynonenal (4-HNE), an electrophilic product of lipid peroxidation in cellular membranes during oxidative stress. 4-HNE is a direct activator of nuclear factor (erythroid-derived 2)-like 2 (Nrf2), a transcription factor with many target genes encoding antioxidant and anti-electrophile enzymes. This is a mechanism by which Gsta4 protects mitochondrial morphology. Radiation impacts mitochondrial morphology and an inactive or loss of function in Gsta4 increases susceptibility to mitochondrial damage due to irradiated cardiac cells. Therefore, increased expression of Gsta4 (e.g., by administering a nitroxide antioxidant to a human subject in need thereof) can promote proper function of the encoded enzyme and ultimately protection of mitochondria in cardiac cells (Boerma et al. Effects of Local Heart Irradiation in a Glutathione S-Transferase Alpha 4-Null Mouse Model. *Radiation Research* (2015) 183(6): 610-619. doi .org/10.1667/RR13979.1; the content of which is incorporated herein in its entirety).

GST genes respond to endogenous factors to decrease intracellular toxicity through conjugation of the endogenous factor with GSH. GST gene activity is adaptive such that different familial gene subunits work to compensate for loss of function or inactive gene activity. Knockout of mouse Gsta4 and Gstz1 leads to overexpression of transferases in the GST Alpha, Mu, and Pi classes, an observation suggesting they are part of an adaptive mechanism that responds to endogenous chemical cues such as 4-hydroxynonenal and tyrosine degradation products. The promoters of cytosolic GST and MAPEG genes contain antioxidant response elements through which they are transcriptionally activated during exposure to Michael reaction acceptors and oxidative stress (Hayes, et al. Glutathione Transferases. Annual Review of Pharmacology and Toxicology. 45:51-88; the content of which is incorporated herein in its entirety).

Gstt1

Glutathione S-transferase theta 1 (Gstt1) is a member of a superfamily of proteins that catalyze the conjugation of reduced glutathione to a variety of electrophilic and hydrophobic compounds. Studies have identified specific indication of Gstt1 in susceptibility to Alzheimer's disease (AD), motor neuron disease (MND) and Parkinson's disease (PD). For example, males with a deletion of the Gstm1 gene were more susceptible to PD, and males with a deletion of the Gstt1 gene were more susceptible to MND and PD, possibly indicating that environmental factors which specifically target men may be involved. Furthermore, subjects with a deletion of the Gstt1 gene were more susceptible to AD (Maudy. Determination of glutathione S-transferase µ and τ polymorphisms in neurological disease. Human & Experimental Toxicology. (1999) 18(3):141-145. doi.org/10.1177/096032719901800302; the disclosure of which is incorporated herein in its entirety).

The combination of heavy smoking and a deletion polymorphism in Gstt1 has been shown to be associated with an increased risk of pancreatic cancer among Caucasians, with the associations possibly stronger in women than in men (Duell, E. J., et al., A population-based, case-control study of polymorphisms in carcinogen-metabolizing genes, smoking, and pancreatic adenocarcinoma risk. *Natl. Cancer Inst.* (2002); the disclosure of which is incorporated herein in its entirety). Increasing an expression level of a Gstt1 encoding gene has been shown to correlate directly with an increase in the concentration of Gstt1 and thereby Gstt1 ability to address oxidative stress induced by heavy smoking.

Myoclonus epilepsy is attributable to oxidative stress and a decreased function of GST enzymes. In particular, decreased or null Gstt1 activity in the presence of oxidative stress has increased susceptibility to progressive myoclonus epilepsy (PME). It has been found that carriers of combined Gsta1-active and Gstt1-null genotype were at a higher risk, 7.55-fold increased risk of PME. Byproducts of protein damage did not reach statistical significance, while superoxide dismutase (SOD) and glutathione peroxidase (GPx) activities were significantly higher in PME patients then in controls. When stratified according to GST genotype, P-SH groups were significantly lower only in patients with Gstt1-null genotype in comparison to carriers of active genotype. Thus, Gstt1 inactivity may increase susceptibility to progressive myoclonus epilepsy (Ercegovac et al. GSTA1, GSM1, GSTP1 and GSTT1 polymorphisms in progressive myoclonus epilepsy: A Serbian case-control study. Seizure (2015) 32:30-6. doi: 10.1016/j.seizure.2015.08.010; the content of which is incorporated herein in its entirety).

Gstt2

Glutathione S-transferase theta 2 (Gstt2) encodes a Gstt2 protein, which is a member of a superfamily of proteins that catalyze the conjugation of reduced glutathione to a variety of electrophilic and hydrophobic compounds. The theta class includes Gstt1, Gstt2, and Gstt2B. Gstt2 and Gstt2B are nearly identical to each other, and share 55% amino acid identity with Gstt1. All three genes may play a role in human carcinogenesis. The Gstt2 gene is a pseudogene in some populations.

As with other conditions described herein, inactivity or decreased activity including decreased enzyme concentration of one or more of the GST enzymes has been found to be predictive of risk or prognosis of the condition. Polymorphisms in the gene encoding Gstt2 has been found to be predictive of an individual's risk of colorectal cancer. Again, polymorphisms relate to the decreased activity or inactivity of the relative enzymes encoded by the polymorphic gene. Increasing expression level of a gene, even where the gene is polymorphic, resulting in decreased expression, increases overall output and function of the enzyme for which the gene encodes. Gstt2 exhibits high glutathione peroxidase activity with cumene hydroperoxide as a substrate. In human colon cancer cells, butyrate and flavonoids that contribute to detoxification of dietary carcinogens induce upregulation of Gstt2 to protect against toxic products of oxygen and lipid peroxidation. This gene may have an important role in carcinogenesis and sensitivity of tumors against oxidation stress. Gstt2 promoter polymorphisms significantly reduce luciferase activity in two human cell lines (HEK239t and TE671). SNPs or mutations within the promoter region reportedly affect transcription activity and gene expression. Therefore, SNPs and haplotypes of the Gstt2 promoter region result in distinct Gstt2 activities, and the −537A allele may be associated with cancer development arising from oxidation stress (Jang et al. Gstt2 promoter polymorphisms and colorectal cancer risk. BMC Cancer (2007) 20077:16. doi.org/10.1186/1471-2407-7-16; the content of which is incorporated herein in its entirety).

Gstp1

Glutathione S-transferase pi 1 (Gstp1) is a polymorphic gene, encoding active, functionally different Gstp1 variant proteins that function in xenobiotic metabolism and play a role in susceptibility to cancer, and other diseases.

Gstp1 has been characterized as a Jun kinase (JNK) inhibitor and Gstm1 binds to and inhibits the activity of ASK1. JNK has been implicated in pro-apoptotic signaling and ASK1 is an MAP kinase kinase. The mechanism of action involves activation of JNK, initiated by the phosphorylation of c-Jun which in turn results in subsequent activation of downstream effectors. During non-stressed condition, there is low JNK catalytic activity due to its sequestration within the protein complex including at least Gstp1 and JNK (Nissar et al. Glutathione S Transferases: Biochemistry, Polymorphism and Role in Colorectal Carcinogenesis. *J Carcinog Mutagen* (2017) 8:287. doi:10.4172/2157-2518.1000287; the content of which is incorporated herein in its entirety).

Gstp1, as with others of the GST gene family, encodes a Phase II enzyme playing a critical role in cellular protection against carcinogens. A non-limiting example of Gstp1 in this regard relates to Hepatocellular Carcinoma (HCC). Polymorphisms in the Gstp1 gene result in decreased activity of the Gstp1 enzyme. Genetic polymorphism has been reported to be a factor increasing the risk of HCC. Phase II enzymes, such as Gstp1 and Gsta1, play important roles in protecting cells against damage induced by carcinogens. Individuals aged ≤57 years with AG or GG alleles of Gstp1 had a 2.18-fold (95% CI=1.09-4.36; p=0.02) and 5.64-fold (95% CI=1.02-31.18; p=0.04) risk, respectively, of developing HCC compared to individuals with AA alleles, after adjusting for other confounders. AG and GG alleles of Gstp1 gene polymorphisms may be considered as factors increasing the susceptibility to and risk of HCC in Taiwanese aged ≤57 years (Chen et al. Glutathione S-Transferase P1 (Gstp1) gene polymorphism increases age-related susceptibility to hepatocellular carcinoma. *BMC Medical Genetics* (2010) 11, 46. doi.org/10.1186/1471-2350-11-46; the content of which is incorporated herein in its entirety).

Gstp1 is commonly inactivated by somatic CpG island hypermethylation in cancers of the prostate, liver, and breast. Hypermethylation of CpG dinucleotides at the 5' transcriptional regulatory region has been shown to be sufficient to inhibit Gstp1 transcription in MCF-7 breast cancer cells and that repression of Gstp1 transcription was mediated in part by the methyl-CpG-binding domain (MBD) protein MBD2. MCF-7 breast cancer cells contained only hypermethylated Gstp1 CpG island alleles and failed to express Gstp1 mRNA or Gstp1 polypeptides (Lin et al. Methyl-CpG-binding domain protein-2 mediates transcriptional repression associated with hypermethylated Gstp1 CpG islands in MCF-7 breast cancer cells. *Cancer Res.* (2003); the content of which is incorporated herein in its entirety).

Gstp1, as with other GST genes and their associated enzymatic activity, has been found to modulate susceptibility regarding various types of cancer (Jourenkova-Mironova et al. Glutathione S-transferase GSTM1, GSTM3, GSTP1 and GSTT1 genotypes and the risk of smoking-related oral and pharyngeal cancers. *Int. J. Cancer* (1999); the content of which is incorporated herein in its entirety). Further, Gstp1 has been shown to increase resistance to doxorubicin in cell lines (Harbottle et al. Role of glutathione S-transferase P1, P-glycoprotein and multidrug resistance-associated protein 1 in acquired doxorubicin resistance. *Int. J. Cancer* (2001); the content of which is incorporated herein in its entirety).

Gstp1 has also been shown to interact with Fanconi anemia complementation group C (FANCC). Overexpression of both proteins in a myeloid progenitor cell line can prevent apoptosis following factor deprivation. FANCC increases Gstp1 activity after the induction of apoptosis. Gstp1 is an enzyme that catalyzes the detoxification of xenobiotics and by-products of oxidative stress, and Gstp1 is frequently upregulated in neoplastic cells. Although FANCC lacks homology with conventional disulfide reductases, it functions by preventing the formation of inactivating disulfide bonds within Gstp1 during apoptosis. The prevention of Gstp1 protein oxidation by FANCC reveals a mechanism of enzyme regulation during apoptosis and has implications for the treatment of degenerative diseases with thiol reducing agents (Cumming et al. Fanconi anemia group C protein prevents apoptosis in hematopoietic cells through redox regulation of GSTP1. *Nat. Med.* (2001); the content of which is incorporated herein in its entirety).

Gstp1 allelic variants resulted in decreased enzymatic activity and increased susceptibility to neurodegenerative diseases such as Parkinson's Disease (PD). One study has identified the polymorphism Gstp1-Alw26I, when related to tobacco use and alcoholism, was the same in the SG, SSG and CG groups, as well as in other studies involving smoking and PD. On the other hand, there are references of tobacco protection in PD, including haplotypes of Gstp1. The catalytic efficiency of the Gstp1 variants differs from that of the wild type, and it varies according to the characteristics of the substrates. This explains the protective effect of the mutant allele regarding diol epoxides found in tobacco products, in contrast with its reduced effects upon detoxification of pesticides. There was an association between smoking and wild homozygote genotype in familial PD patients (Longo. Exposure to pesticides and heterozygote genotype of Gstp1-Alw26I are associated to Parkinson's disease. *Arq. Neuro-Psiquiatr.* (2013) 71(7); the content of which is incorporated herein in its entirety).

Gstk1

Glutathione S-transferase kappa 1 (Gstk1) is a member of the kappa class of the GST gene family.

Aging is often associated with a number of conditions and diseases. A natural byproduct of aging is a decreased function of certain tissues and biological processes leading to increased susceptibility of diseases and conditions. Further, aging results in a decrease in expression of one or more GSTs. For example, hypertrophic cardiomyopathy (HCM) is characterized by left ventricular hypertrophy and is associated with a number of potential outcomes, including impaired diastolic function, heart failure, and sudden cardiac death. Gstk1 has been identified as dysregulated and specifically downregulated in HCM. A study on murine models identified five mouse HCM models of differing etiology: (i) mutation of myosin heavy chain 6, (ii) mutation of tropomyosin 1, (iii) expressing human phospholamban on a null background, (iv) knockout of frataxin, and (v) transverse aortic constriction. Gene-by-gene comparison identified five genes dysregulated in all five HCM models. Gstk1 was significantly downregulated in the five models. Further, Gstk1 knockout resulted in significantly decreased the end diastolic volume and, to a lesser extent, end systolic volume as Gstk1 disregulation is implicated as an underlying cause of HCM (Sasagawa et al. Downregulation of GSTK1 Is a Common Mechanism Underlying Hypertrophic Cardiomyopathy. *Frontiers in Pharmacology* (2016) 7, 162. doi.org/10.3389/fphar.2016.00162; the content of which is incorporated herein in its entirety).

Combined Decreased Expression of More than One Glutathione S-Transferase

In some embodiments, pathogenesis of a disease or occurrence of a condition is exacerbated by a polymorphism or lack of or downregulation of more than one Glutathione S-transferase encoding gene. For example, susceptibility to cancer is increased in individuals with a polymorphic genotype relating to GST genes. Although only a moderate risk of breast cancer was seen for premenopausal women concurrently carrying the Gstm3*B allele containing genotypes and the Gstp1 Ile/Ile genotype (OR, 2.07; 95% CI, 1.02-4.18), the risk rose steeply if they simultaneously lacked the Gstt1 gene (OR, 9.93, 95% CI, 1.10-90.0). A borderline significant increase in the risk of breast cancer was also observed for premenopausal women with the combination of Gstm1 null, Gstp1 Ile/Ile, and Gstt1 null genotypes (OR, 3.96; 95% CI, 0.99-15.8). Such findings support that GST genotypes contribute to the individual breast cancer risk, for example, in certain combinations (Katja et al. Glutathione S-Transferase M1, M3, P1, and T1 Genetic Polymorphisms and Susceptibility to Breast Cancer. Cancer Epidemiol. Biomarkers Prev. (2001) 10(3):229-236; the content of which is incorporated herein in its entirety.).

Another non-limiting example of polymorphism mediated pathogenesis of a disease involving more than one GST gene is lung disease. Gstm1, Gstm3, Gstp1, and Gstt1 have been found to increase the severity of lung disease in some patient populations. Specifically, polymorphism of the Gstm3 gene contributes to clinical severity in cystic fibrosis (CF), which may have prognostic significance and could prompt to start a more targeted therapy in young patients with CF (Flamant C, Henrion-Caude A, Boelle P Y, et al. Glutathione-S-transferase M1, M3, P1 and T1 polymorphisms and severity of lung disease in children with cystic fibrosis. Pharmacogenetics (2004) 14:295-301; the content of which is incorporated herein in its entirety).

Head and neck squamous cell carcinoma (HNSCC) is attributable to various environmental and exogenous factors combined with decreased activity of GST genes (Gstm1, Gstt1 and Gstp1). The inactivity of these genes in the presence of environmental factors, such as tobacco and alcohol, marked a notable increase in the susceptibility to HNSCC. Statistical analysis showed an increase in risk to HNSCC in patients with null genotype of Gstm1 (OR: 2.02; 95% CI: 1.32-3.10; P=0.001) or Gstt1 (OR: 1.66; 95% CI: 1.02-2.69; P=0.04). The risk may not be significant when adjusted for age, sex, smoking, tobacco chewing or alcohol use by multivariate logistic regression model. Combination of deletion genotypes of GST (Gstm1 and Gstt1) can confer an even higher risk of HNSCC. Interestingly, Gstp1 wild type genotype in combination with Gstm1 null or Gstt1 null genotype increased susceptibility for HNSCC (OR: 2.49 and 2.75, respectively). Likewise a much greater risk for HNSCC was observed in the patients carrying a genotype combination of Gstm1 null, Gstt1 null and Gst1 (Ile/Ile) (OR: 4.47; 95% CI: 1.62-12.31; P=0.002). The interaction between tobacco chewing and null genotype of Gstm1 or Gstt1 resulted in about 3.5- and 2.2-fold increase in the risk respectively in the patients when compared to those not chewing tobacco. Alcohol use resulted in more than 4-fold increase in the risk in the patients with null genotype of Gstm1 as compared to those who are non-drinkers. Alcohol consumption also increased the risk (approx. 3-fold) in the cases with null genotype of Gstt1 (Madhu et al. Association of genetic polymorphisms in glutathione S-transferases and susceptibility to head and neck cancer, Mutation Research/Fundamental and Molecular Mechanisms of Mutagenesis (2008) 638(1-2): 184-194. doi.org/10.1016/j.mrfmmm.2007.10.003; the content of which is incorporated herein by reference in its entirety).

Another non-limiting example of combined gene interaction relating to a particular condition is blood disorders, such as sickle cell disease. Clinical manifestations of sickle cell disease (SCD) result from sickling of hemoglobin S (HbS) due to oxidation, which is augmented by accumulation of oxygen-free radicals (Ellithy et al. Relation between glutathione S-transferase genes (Gstm1, Gstt1, and Gstp1) polymorphisms and clinical manifestations of sickle cell disease in Egyptian patients. Hematology (2015) 20(10):598-606; the content of which is incorporated herein in its entirety). Decreased or inactivity of GST genes was found to worsen clinical manifestation of SCD. Therefore, increasing expression of one or more of the GST genes can improve the clinical manifestations of a blood disorder associated with (e.g., defined by) decreased or inactive function of one or more GST enzymes.

Protection Against Toxicity from Exogenous Factors

GST enzymatic activity, among other things, is directed to facilitating the prevention of toxicity based on one or more xenobiotics within the cell. Xenobiotics can encompass foreign bodies within the cell reactive oxygen species (ROS), pharmaceutical compounds, environmental factors, and endogenous compounds such as resulting ROS as a negative response to extracellular stimuli. Non-limiting examples of xenobiotics may include halocarbons, poly chlorinated biphenyls, synthetic polymers, alhylhenzyl sulphonates, oil mixtures, pesticides, etc.

In some embodiments, xenobiotics require redox reactions to form the reactive intermediates involved in the ultimate toxic events (e.g., adduct formation). The same mechanisms lead to the formation of reactive oxygen species, which can themselves exert direct toxicity including, e.g., DNA oxidative damage or glutathione depletion (Pagano. Redox-modulated xenobiotic action and ROS formation: a mirror or a window? Human and Experimental Toxicology (2002) 21(2):77-81; the content of which is incorporated herein in its entirety).

Exogenous factors such as chemotherapeutic agents and radiation are commonly administered to patients as treatment for cancer and autoimmune diseases. The broad spectrum of effect of such factors results in a non-specific target for the chemotherapeutic agents, thereby resulting in significant damage to healthy cells. Often, the chemotherapeutic agents are dose limited due to the devastating effects on healthy tissues. The significance of the effect on healthy tissue manifests in permanent tissue damage and loss of function or death from administration of the chemotherapeutic agents.

Radiation is commonly used as a treatment for conditions such as cancer. Radiation allows for a more focused application of treatment to target tissues with less collateral damage than chemotherapeutic agents. However, collateral damage to surrounding tissues and cells results from radiation administration. Increased levels of antioxidants before the initiation of radiotherapy may improve the tolerability of normal cells to cope up with the radiation stress and may serve as biomarkers in patients (e.g., cancer or HNSCC patients) who may undergo radiotherapy. Polymorphisms in these antioxidant and detoxification genes can decrease the activity of the particular enzyme. Increased phase I clearance of toxic agents can exert pressure on phase II activity. In turn, reduced phase II activity can lead to the toxic intermediates. Similarly, reduced phase I activity can cause accumulation of toxins. Adverse reactions seen in case of radiation/chemotherapy may be due to a decreased capacity for clearing the toxins as well as intermediates from the system. Further, studies have indicated that glutathione levels can be a prognostic marker for radiation therapy in patients with cancers, such as cervical cancer. Plasma glutathione is also associated with the outcome of head and neck cancer (HNC) post radiotherapy treatment. Gstp1 has been found to have a significant association with a higher risk of radiation-induced, fibrosis in breast cancer patients as well as acute skin toxicity (Goutham et al. Genotype-phenotype association of TGF-β1 and GST with chemoradiotherapy induced toxicity. International Journal of Radiation Research (2017) 15(1); the content of which is incorporated herein by reference in its entirety).

In some embodiments, the nitroxide antioxidant selectively protects non-cancer cells from deleterious and damaging effects of chemotherapeutic agents. For example, administration of a nitroxide antioxidant such as Tempol to a subject (e.g., a human subject) increases expression of the one or more glutathione S-transferase in the non-cancer cells of the subject. Where the nitroxide antioxidant operates through a cyclical mechanism in which the original nitroxide is regenerated, hypoxic cells such as tumor cells can inhibit the cyclic nature of the nitroxide and arrests the reaction at an intermediate step of hydroxylamine. The prevention of a complete cycle of the nitroxide mechanism (including regeneration of the original nitroxide) may prevent the enzymatic activity of a GST to conjugate GSH with the xenobiotic, resulting in increased intracellular toxicity and ultimately cell death. In an embodiment, cancer cells of a tumor would inhibit the increased expression of Gstm3, Gstm6, Gsta3, Gstt1, Gsta4, Gstm1, Gstm4, Gstt2, Gstp1, Gstk1, or any combination thereof. Non-cancer cells support regeneration of the original nitroxide antioxidant and therefore more effectively produce an increase in the expression of Gstm3, Gstm6, Gsta3, Gstt1, Gsta4, Gstm1, Gstm4, Gstt2, Gstp1, Gstk1, or any combination thereof. The increased expression of these genes reduces or prevents chemotherapeutic-induced toxicity. This ultimately results in selective protection of supportive non-cancer cells and a simultaneous mediation of the desired effects of the chemotherapeutic agents within cancer cells.

In some embodiments, the nitroxide antioxidant selectively protects cells from deleterious and damaging effects of radiation. For example, administration of a nitroxide antioxidant such as Tempol to a subject increases expression of the one or more glutathione S-transferases in the cells of the subject. Where the nitroxide oxidant operates through a cyclical mechanism, hypoxic cells such as tumor cells inhibit the cyclic nature of the nitroxide mechanism and arrests the reaction at an intermediate step of hydroxylamine. The prevention of a complete cycle of the nitroxide mechanism may prevent the enzymatic activity to conjugate GSH with the xenobiotic resulting in increased intracellular toxicity and ultimately cell death. In such an embodiment, cancer cells such as a tumor would inhibit the increased expression of Gstm3, Gstm6, Gsta3, Gstt1, Gsta4, Gstm1, Gstm4, Gstt2, Gstp1, Gstk1, or any combination thereof. Non-cancer cells support cycling of the nitroxide antioxidant and therefore increase in the expression of Gstm3, Gstm6, Gsta3, Gstt1, Gsta4, Gstm1, Gstm4, Gstt2, Gstp1, Gstk1, or any combination thereof. The increased expression of these genes reduces or prevents radiation-induced toxicity. This can result in selective protection of supportive non-cancer cells and a simultaneous mediation of the desired effects of the radiation within cancer cells.

GST isoenzymes have been shown to detoxify a large number of exogenous substrates, including carcinogens, drugs and environmental pollutants. The cancer chemotherapeutic agents are also detoxified by GSH-like adriamycin, 1,3-bis (2-chloroethyl)-1-nitrosourea (BCNU), busulfan, carmustine, chlorambucil, cis-platin, crotonyloxymethyl-2-cyclohexenone (COMC-6), melphalan, mitozantrone, and thiotepa, cyclophosphamide, ethacrynic acid. Environmental chemicals and their metabolites detoxified by GST include acrolein, atrazine, DDT, inorganic arsenic, lindane, malathion, methyl parathion, muconaldehyde, and tridiphane. A large number of epoxides, such as the antibiotic fosfomycin and those derived from environmental carcinogens, polycyclic aromatic hydrocarbons (PAHs) etc are detoxified by GST. Activated metabolite, N-acetoxy-PhIP of heterocyclic amine, 2-amino-1-methyl-6-phenylimidazo[4,5-b]pyridine (PhIP), produced by cooking protein-rich food is also detoxified by cytosolic GST isoenzymes (Nissar et al. (2017). Further, As a result of oxidative stress, the reactive oxygen species, the superoxide anion $O^{-2}$, hydrogen peroxide $H_2O_2$, and the hydroxyl radical HO. inflict damage on DNA (e.g., directly or indirectly) on membrane lipid, protein, and carbohydrate. Free radicals arising primarily through oxidative phosphorylation and other oxidase-catalyzed reactions are scavenged by the catalytic activities of superoxide dismutase, catalase and glutathione peroxidase and non-enzymatically by α-tocopherol, ascorbic acid, GSH, and bilirubin. Moreover the by-products of oxidative stress are tackled by number of enzymes like Aldehyde dehydrogenase, alcohol dehydrogenase, aldo-keto reductase, GST, and Selenium-dependent glutathione peroxidase (GPx) (Nissar et al. (2017).

Administration of a nitroxide antioxidant to a subject can selectively upregulate GST expression and thereby GST activity of associated and encoded proteins, enzymes, and cofactors, in healthy cells and normal tissues. A non-limiting example is illustrated as Gstm1 copy number variant was inversely associated with survival in colorectal cancer patients treated with chemotherapy. Mortality was significantly reduced in patients with one Gstm1 copy (hazard ratio: 0.45, 95% CI: 0.23-0.90, p=0.02) and nonsignificantly reduced in those with the null genotype (HR: 0.67, 95% CI: 0.35-1.27, p=0.22) compared with carriers of two copies (Funke et al. Genetic polymorphisms in GST genes and survival of colorectal cancer patients treated with chemotherapy Pharmacogenomics (2010) 11(1):33-41. doi: 10.2217/pgs.09.132; the content of which is incorporated herein in its entirety).

In some embodiments, the exogenous factor is cisplatin or cisplatin-like molecules. Cisplatin is a widely used antitumor agent associated with negative side effects such as nephrotoxicity, neurotoxicity and ototoxicity. Cisplatin targets DNA synthesis and inhibits RNA transcription. Associated ototoxicity is a result of increased concentration of free radicals in cochlear tissue. The increased free radical concentration is compounded by the combined cisplatin-induced decrease in antioxidant enzymes such as the GST family of enzymes.

Free Radicals Produced by Oxidative Stress

When the production of reactive oxygen exceeds the natural threshold of the body's capability to address the reactive intermediates, resulting free radicals exist and mediate a variety of diseases and conditions such as aging, diabetes, cardiovascular disease, cancer, immune function, metabolism, and neurodegeneration. Oxidative stress can be seen as a general term to refer to this mechanism of production of free radicals and the resulting conditions therefrom. The free radicals are addressed in a similar way to other xenobiotics as a cell would attempt to neutralize the free radicals.

Both endogenous and exogenous factors contribute to an imbalance in cellular metabolism resulting in production of free radicals. Of these factors, a compounding issue is the effect they have to inhibit GST activity. Arsenic is a highly toxic element that produces a variety of ROS, including superoxide ($O_2.^-$), singlet oxygen ($O_2(^1\Delta g)$), peroxyl radical (ROO.), nitric oxide (NO.), hydrogen peroxide (H2O2), and dimethylarsinic peroxyl radicals (($CH_3)_2AsOO.$). Arsenic (III) compounds can inhibit antioxidant enzymes, including the GSH-dependent enzymes, such as glutathione-S-transferases (GSTs), glutathione peroxidase (GSH-Px), and GSH reductase, via binding to their sulfhydryl (—SH) groups. Lead increases lipid peroxidation. Significant decreases in the activity of tissue superoxide dismutase (SOD) and brain GPx have been reported after lead exposure. Replacement of zinc, which serves as a cofactor for many enzymes by lead, leads to inactivation of such enzymes. Lead exposure may cause inhibition of GST by affecting tissue thiols (Birben et al. Oxidative Stress and Antioxidant Defense. The World Allergy Organization Journal. (2012) 5(1), 9-19. http://doi.org/10.1097/WOX.0b013e3182439613; the content of which is incorporated herein in its entirety). Therefore, increasing expression of one or more GST encoding genes overcomes the inhibitory effects of these factors promoting increased, improved, and effective GST detoxification activity.

Aging is associated with increased oxidative stress. In certain neurons, "glutathione-mediated detoxification" and "glutathione redox reactions" were among the top gene pathways altered with age (including the genes Gsta3, Gsta4, Gstm1, Gstm6, Gpx1, Gpx2, and Gpx6). Oxidative damage has been linked to aging. Oxidative damage to DNA, proteins, and lipids has been reported to increase with age in the brain (Shema et al. Synthetic lethal screening in the mammalian central nervous system identifies Gpx6 as a modulator of Huntington's disease. Proceedings of the National Academy of Sciences of the United States of America (2014) 112(1):268-272. doi: 10.1073/pnas.1417231112; the content of which is incorporated herein in its entirety).

Methods for Counteracting Decrease in Gene Expression or Treating a Condition

Some embodiments disclosed herein provide methods for counteracting age-related decrease in gene expression or treating an age-related disease, comprising identifying a human subject over the age of 35 and having a decreased expression level of one or more genes associated with glutathione S-transferase or an age-related disease; and administering to the human subject an effective amount of a nitroxide antioxidant. In some embodiments, the methods comprise determining the expression level of one or more genes associated with glutathione S-transferase. However, this may not be necessary in some instances, such as where a decreased expression level of one or more genes associated with glutathione S-transferase can be inferred from the human subject's age, family history, health conditions, medical history, habits, or a combination thereof. In some embodiments, the methods disclosed herein may be used to treat a human subject shows no symptoms of an age-related disease, but is at risk of having an age-related disease. Exemplary risk factors for an age-related disease include, but are not limited to, age, family history, health conditions, medical history, habits, or a combination thereof. In some embodiments, risk factors for an age-related disease comprise a decreased expression level of one or more genes associated with glutathione S-transferase.

In some embodiments, administering to the human subject an effective amount of the nitroxide antioxidant results in an increased expression level of a gene, for example a gene associated with glutathione S-transferase. The gene associated with glutathione S-transferase can be Gstm3, Gstm6, Gsta3, Gstt1, Gsta4, Gstm1, Gstm4, Gstt2, Gstp1, or Gstk1. The treatment of the human subject with the effective amount of the nitroxide antioxidant can result in an increased expression level of the gene. For example, the treatment can result in increased expression levels of Gstm3, Gstm6, Gsta3, Gstt1, Gsta4, Gstm1, Gstm4, Gstt2, Gstp1, Gstk1, or any combination thereof. The increased expression levels of Gstm3, Gstm6, Gsta3, Gstt1, Gsta4, Gstm1, Gstm4, Gstt2, Gstp1, Gstk1, or any combination thereof, can increase the level of apoptosis. The increased level of apoptosis can result in a decrease in or disappearance of signs and symptoms of an age-related disease associated with decreased apoptosis, including the curing of the age-related disease. In some embodiments, the increased expression levels of Gstm3, Gstm6, Gsta3, Gstt1, Gsta4, Gstm1, Gstm4, Gstt2, Gstp1, Gstk1, or any combination thereof, can decrease the level of apoptosis. The decreased level of apoptosis can result in a decrease in or disappearance of signs and symptoms of the age-related disease associated with increased apoptosis, including the curing of the disease associated with age-related disease associated with increased apoptosis.

In some embodiments, the levels of Gstm3, Gstm6, Gsta3, Gstt1, Gsta4, Gstm1, Gstm4, Gstt2, Gstp1, Gstk1, or any combination thereof in the connective tissue, muscle tissue, nervous tissue, or epithelial tissue may change after the nitroxide antioxidant is administered. Non-limiting examples of the connective tissue include dense connective tissue, loose connective tissue, reticular connective tissue, adipose tissue, cartilage, bone, and extracellular matrix. Non-limiting examples of the muscle tissue includes smooth muscle tissue, cardiac muscle tissue, and skeletal muscle tissue. Non-limiting examples of the nervous tissue include neural tissue of the central nervous system, neural tissue of the peripheral nervous system, the brain, spinal cord, cranial nerves, spinal nerves, and motor neurons. Non-limiting examples of the epithelial tissue include squamous epithelium, cuboidal epithelium, columnar epithelium, glandular epithelium, ciliated epithelium, and skin.

Some embodiments disclosed herein provide methods for treating a disease related to aging in a human subject in need thereof, comprising identifying a human subject over the age of 35 and having an age-related disease and having a decreased expression level of a gene associated with glutathione S-transferase; and administering to the human subject an effective amount of a nitroxide antioxidant. Some embodiments disclosed herein provide methods for treating an individual having or at risk of developing a condition due to aging, comprising: identifying an individual over the age of 35; and administering to the individual an effective amount of a nitroxide antioxidant, whereby the expression level of the gene associated with glutathione S-transferase is increased.

Non-limiting examples of age-related diseases include cancer, rheumatoid/osteoid arthritis, systemic lupus erythematosus (SLE), inflammatory bowel disease, Alzheimer's disease, multiple sclerosis, atherosclerosis, cardiovascular disease, cataracts, dementia, osteoporosis, type 2 diabetes, hypertension.

Methods for Increasing Expression Level of a Gene

Some embodiments disclosed herein provide methods for increasing the expression level of a gene in a human subject in need thereof, comprising identifying a human subject having a decreased expression level of a gene associated with glutathione S-transferase; and administering to the human subject an effective amount of a nitroxide antioxidant. Some embodiments disclosed herein provide methods for treating a disease associated with a decreased apoptosis in a patient in need thereof, comprising identifying a human subject having a decreased expression level of a gene associated with glutathione S-transferase; and administering to the human subject an effective amount of a nitroxide antioxidant. The decreased expression level may be age-related, or disease related. In some embodiments, the disease may be cancer, rheumatoid/osteoid arthritis, systemic lupus erythematosus (SLE), inflammatory bowel disease, Alzheimer's disease, multiple sclerosis, atherosclerosis, cardiovascular disease, cataracts, dementia, osteoporosis, type 2 diabetes, hypertension, or any combination thereof. Some embodiments disclosed herein provide methods for treating an individual in need thereof, comprising identifying a human subject over the age of 35 in need of an increased expression level of a gene associated with glutathione S-transferase; and administering to the human subject an effective amount of a nitroxide antioxidant. In some embodiments, the methods comprise determining the expression level of one or more genes associated with glutathione S-transferase. However, this may not be necessary in some instances, such as where a decreased expression level of one or more genes associated with glutathione S-transferase can be inferred from the human subject's age, family history, health conditions, medical history, habits, or a combination thereof. In some embodiments, the methods disclosed herein may be used to treat a human subject shows no symptoms of a disease associated with a decreased apoptosis, but is at risk of having a disease associated with a decreased apoptosis. Exemplary risk factors for a disease associated with a decreased apoptosis include, but are not limited to, age, family history, health conditions, medical history, habits, or a combination thereof.

In some embodiments, administering to the human subject an effective amount of the nitroxide antioxidant results in an increased expression level of a gene, for example a gene associated with glutathione S-transferase. The gene associated with glutathione S-transferase can be Gstm3, Gstm6, Gsta3, Gstt1, Gsta4, Gstm1, Gstm4, Gstt2, Gstp1, or Gstk1. The treatment of the human subject with the effective amount of the nitroxide antioxidant can result in an increased expression level of the gene. For example, the treatment can increase the expression levels of Gstm3, Gstm6, Gsta3, Gstt1, Gsta4, Gstm1, Gstm4, Gstt2, Gstp1, Gstk1, or any combination thereof. The increased expression of the gene counteracts the decrease in the expression level of the gene.

Methods for Preventing or Treating Cancer

Some embodiments disclosed herein provide methods for preventing cancer in a human subject, comprising identifying a human subject in need of an increased expression level of a gene associated with glutathione S-transferase; and administering to the human subject an effective amount of a nitroxide antioxidant. In some embodiments, the methods disclosed herein may be used to prevent cancer development in a human subject showing no symptoms of cancer, but is at risk of having cancer. Exemplary risk factors for cancer include, but are not limited to, age, family history, health conditions, medical history, habits, or a combination thereof.

In some embodiments, risk factors for cancer comprise a decreased expression level of one or more genes associated with glutathione S-transferase.

In some embodiments, cancer development is mediated by unregulated cell growth and dysfunction in proto-oncogenes. Xenobiotics can result in genotoxicity and mutations in DNA sequences involved in the transcription or translation of genes involved in cellular function including cell growth and development. For example, proto-oncogenes are susceptible to mutation through interaction between xenobiotic factors and corresponding DNA sequences. Also known as genotoxic xenobiotics, such xenobiotic substances and factors contribute to the unregulated cell growth and development attributed to carcinogenesis. The accumulation of genetic damages in the forms of activated proto-oncogenes and inactivated tumor-suppressor genes can be the driving force in the evolution of a normal cell to a malignant cell. Activation of the Ras gene is an early event in cancer, such as the "initiating" step—in the development of many chemical-induced rodent tumors. Ras Oncogenes are observed in more human tumors and at a higher frequency than any other oncogene, and activation of the proto-oncogene may occur at various stages of the carcinogenic process (Anderson et al. Role of proto-oncogene activation in carcinogenesis. *Environmental Health Perspectives*, (1992) 98:13-24; the content of which is incorporated herein in its entirety).

Chemical, environmental, endogenous and exogenous factors are or result in the presence of xenobiotics. Increased xenobiotic concentrations correlate with increased occurrence of oncogenes such as Ras. For example, overexpression of the Ras oncogene in plasma was found in the samples taken during winter, suggesting a strong influence of complex exposure caused by domestic coal heating (Silins et al. Combined Toxic Exposures and Human Health: Biomarkers of Exposure and Effect. *International Journal of Environmental Research and Public Health* (2011) 8(3): 629-647. doi.org/10.3390/ijerph8030629; the content of which is incorporated herein in its entirety). Another example of xenobiotic associated carcinogenesis is seen in the mechanisms and toxicological consequences of oxidative stress triggered by metals and dietary or environmental pollutants in general. Besides causing DNA damage, ROS may further induce multiple intracellular signaling pathways, such as NF-κB, JNK/SAPK/p38, as well as Erk/MAPK. These signaling routes can lead to transcriptional induction of target genes that could promote proliferation or confer apoptosis resistance to exposed cells (Henkler et al. The Role of Oxidative Stress in Carcinogenesis Induced by Metals and Xenobiotics. *Cancers* (2010). 2(2):376-396. doi.org/10.3390/cancers2020376; the content of which is incorporated herein in its entirety). Therefore, the regulation and increase of GST activity and the corresponding increase in glutathione activity in addressing xenobiotics, by administration of a nitroxide antioxidant, prevents cancer.

In some embodiments, administering to the human subject an effective amount of the nitroxide antioxidant results in an increased expression level of a gene in the human subject, for example a gene associated with glutathione S-transferase. The gene associated with glutathione S-transferase can be Gstm3, Gstm6, Gsta3, Gstt1, Gsta4, Gstm1, Gstm4, Gstt2, Gstp1, or Gstk1. The treatment of the human subject with the effective amount of the nitroxide antioxidant can result in an increased expression of the gene. For example, the treatment can result in increased expression levels of Gstm3, Gstm6, Gsta3, Gstt1, Gsta4, Gstm1, Gstm4, Gstt2, Gstp1, Gstk1, or any combination thereof.

The increased expression level of the gene can increase the level of GST activity. For example, the increased expression level of the gene can increased capacity of cells to remove xenobiotics and genotoxic xenobiotics. The increased level of GST activity can result in prevention of proto-oncogene mutations to oncogenes and prevention of associated cancer.

Some embodiments disclosed herein provide methods for treating cancer in a human subject in need thereof, comprising identifying a human subject having a cancer and in need of an increased expression level of a gene associated with glutathione S-transferase; and administering to the human subject an effective amount of a nitroxide antioxidant. In some embodiments, the methods disclosed herein may be used to treat a human subject with no symptoms of cancer, but is at risk of having cancer. Exemplary risk factors for cancer include, but are not limited to, age, family history, health conditions, medical history, habits, or a combination thereof. In some embodiments, risk factors for cancer comprise a decreased expression level of one or more genes associated with glutathione S-transferase.

In some embodiments, administering to the human subject an effective amount of the nitroxide antioxidant results in an increased expression level of a gene, for example a gene associated with glutathione S-transferase. The gene associated with glutathione S-transferase can be Gstm3, Gstm6, Gsta3, Gstt1, Gsta4, Gstm1, Gstm4, Gstt2, Gstp1, or Gstk1. The treatment of the human subject with the effective amount of the nitroxide antioxidant can result in an increased expression of the gene. For example, the treatment can result in increased expression levels of Gstm3, Gstm6, Gsta3, Gstt1, Gsta4, Gstm1, Gstm4, Gstt2, Gstp1, Gstk1, or any combination thereof. The increased expression level of the gene can increase the level of apoptosis. The increased level of apoptosis can result in a decrease in or disappearance of signs and symptoms of the cancer, including the curing of the cancer.

In some embodiments, administering to the human subject an effective amount of the nitroxide antioxidant results in an increased expression level of a gene, for example a gene associated with glutathione S-transferase, in non-cancer cells. For example, the nitroxide antioxidant can be arrested in an intermediate state (e.g., a cation intermediate state) in cancer cells. According, the treatment of the human subject with the nitroxide antioxidant does not result in an increased expression of the gene in the cancer cells. In contrast, the treatment of the human subject with the nitroxide antioxidant results in an increased expression level of the gene in non-cancer cells. For example, the treatment can result in increased expression levels of Gstm3, Gstm6, Gsta3, Gstt1, Gsta4, Gstm1, Gstm4, Gstt2, Gstp1, Gstk1, or any combination thereof, in non-cancer cells. The increased expression level of the gene in non-cancer cells can protect non-cancer cells against a chemotherapeutic agent, a xenobiotic. For example, the increased expression level of the gene can increased capacity of non-cancer cells to remove the chemotherapeutic agent and prevent or minimize the effects of the chemotherapy drug in non-cancer cells. In contrast, the cancer cells are not protected against the chemotherapeutic agent because the nitroxide antioxidant, arrested in an intermediate state in cancer cells, may not increase the expression level of the gene in cancer cells. The nitroxide antioxidant can thus selectively protect healthy cells from the effects of a chemotherapeutic agent while allowing the chemotherapeutic agent to effect on cancer cells.

In some embodiments, the chemotherapeutic agent can be, or include, an alkylating agent, an antimetabolite, an anti-tumor antibiotic, a topoisomerase inhibitor, a mitotic inhibitor, a corticosteroid, or any combination thereof. For example, an alkylating agent can be, or include, altretamine, busulfan, carboplatin, carmustine, chlorambucil, cisplatin, cyclophosphamide, dacarbazine, lomustine, melphalan, oxaliplatin, temozolomide, thiotepa, or any combination thereof. For example, an antimetabolite can be, or include, 5-fluorouracil (5-FU), 6-mercaptopurine (6-MP), capecitabine (Xeloda®), cytarabine (Ara-C®), floxuridine, fludarabine, gemcitabine (Gemzar®), hydroxyurea, methotrexate, pemetrexed (Alimta®), or any combination thereof. For example, an anti-tumor antibiotic can be, or include, an anthracycline, such as daunorubicin, doxorubicin (Adriamycin®), epirubicin, idarubicin, or any combination thereof. Examples of an anti-tumor antibiotic include, actinomycin-D, bleomycin, mitomycin-C, mitoxantrone, and any combination thereof. For example, a topoisomerase inhibitor can be, or include, a topoisomerase I inhibitor (such as topotecan and irinotecan (CPT-11)), a topoisomerase II inhibitor (such as etoposide (VP-16), and teniposide, mitoxantrone), or any combination thereof. Examples of a mitotic inhibitor include docetaxel, estramustine, ixabepilone, paclitaxel, vinblastine, vincristine, vinorelbine, and any combination thereof. For example, a corticosteroid can be, or include, prednisone, methylprednisolone (Solumedrol®), dexamethasone (Decadron®), or any combination thereof. In some embodiments, the chemotherapeutic agent can be a platinum-based chemotherapeutic agent (e.g., carboplatin and cisplatin). In some embodiments, the chemotherapeutic agent can be 5-fluorouracil, bleomycin, capecitabine, cisplatin, cyclophosphamide, dacarbazine, doxorubicin, epirubicin, etoposide, folinic acid, methotrexate, mustine, oxaliplatin, prednisolone, procarbazine, vinblastine, vincristine, or any combination thereof. In some embodiments, the chemotherapeutic agent can include, or be conjugated with, an antibody (e.g., a monoclonal antibody).

Non-limiting examples of the methods for identifying a human subject at risk for or having cancer include colonoscopy; sigmoidoscopy; and high-sensitivity fecal occult blood tests. In some embodiments, methods for identifying a human subject having a cancer include low-dose helical computed tomography; mammography; and pap test and human papillomavirus (HPV) testing. In some embodiments, methods for identifying a human subject having a cancer include alpha-fetoprotein blood test; breast magnetic resonance imaging (MRI); CA-125 test; clinical breast exams and regular breast self-exams; prostate-specific antigen (PSA) testing; skin exams; transvaginal ultrasound; and virtual colonoscopy. In some embodiments, methods for identifying a human subject having a cancer include barium enema; biopsy; bone marrow aspiration and biopsy; bone scan; breast MRI for early detection of breast cancer; breast MRI; colonoscopy; computed tomography (CT) scan; digital rectal exam (DRE); blood and platelets testing; bone marrow testing; umbilical cord blood testing; electrocardiogram (EKG) and echocardiogram; endoscopic techniques; fecal occult blood tests; magnetic resonance imaging (MM); mammography; multi gated acquisition (MUGA) scan; papanicolaou (pap) test; positron emission tomography and computed tomography (PET-CT) scan; sigmoidoscopy; tumor marker tests; ultrasound; upper endoscopy. In some embodiments, methods for identifying a human subject having a cancer include DNA sequencing; detecting presence of single nucleotide polymorphism (SNIP); and detecting the presence of certain protein markers.

Non-limiting examples of cancer include bladder and other urothelial cancers; breast cancer; cervical cancer;

colorectal cancer; endometrial cancer; endometrial cancer; esophageal cancer; liver (hepatocellular) cancer; lung cancer; neuroblastoma cancer; oral cavity and oropharyngeal cancer; ovarian, fallopian tube, and primary peritoneal cancer; prostate cancer; skin cancer; stomach (gastric) cancer; and testicular cancer.

Non-limiting examples of cancer include acute lymphoblastic leukemia, adult; acute myeloid leukemia, adult; adrenocortical carcinoma; aids-related lymphoma; anal cancer; bile duct cancer; bladder cancer; brain tumors, adult; breast cancer; breast cancer and pregnancy; breast cancer, male; carcinoid tumors, gastrointestinal; carcinoma of unknown primary; cervical cancer; chronic lymphocytic leukemia; chronic myelogenous leukemia; chronic myeloproliferative neoplasms; cns lymphoma, primary; colon cancer; endometrial cancer; esophageal cancer; extragonadal germ cell tumors; fallopian tube cancer; gallbladder cancer; gastric cancer; gastrointestinal carcinoid tumors; gastrointestinal stromal tumors; germ cell tumors, extragonadal; germ cell tumors, ovarian; gestational trophoblastic disease; hairy cell leukemia; hepatocellular (liver) cancer, adult primary; histiocytosis, langerhans cell; hodgkin lymphoma, adult; hypopharyngeal cancer; intraocular (eye) melanoma; islet cell tumors, pancreatic neuroendocrine tumors; kaposi sarcoma; kidney (renal cell) cancer; kidney (renal pelvis and ureter, transitional cell) cancer; langerhans cell histiocytosis; laryngeal cancer; leukemia, adult acute lymphoblastic; leukemia, adult acute myeloid; leukemia, chronic lymphocytic; leukemia, chronic myelogenous; leukemia, hairy cell; lip and oral cavity cancer; liver cancer, adult primary; lung cancer, non-small cell; lung cancer, small cell; lymphoma, adult Hodgkin; lymphoma, adult non-hodgkin; lymphoma, aids-related; lymphoma, primary cns; malignant mesothelioma; melanoma; melanoma, intraocular (eye); merkel cell carcinoma; metastatic squamous neck cancer with occult primary; multiple myeloma and other plasma cell neoplasms; mycosis fungoides and the sézary syndrome; myelodysplastic syndromes; myelodysplastic/myeloproliferative neoplasms; myeloproliferative neoplasms, chronic; paranasal sinus and nasal cavity cancer; nasopharyngeal cancer; neck cancer with occult primary, metastatic squamous; non-hodgkin lymphoma, adult; non-small cell lung cancer; oral cavity cancer, lip oropharyngeal cancer; ovarian epithelial cancer; ovarian germ cell tumors; ovarian low malignant potential tumors; pancreatic cancer; pancreatic neuroendocrine tumors (islet cell tumors); pheochromocytoma and paraganglioma; paranasal sinus and nasal cavity cancer; parathyroid cancer; penile cancer; pheochromocytoma and paraganglioma; pituitary tumors; plasma cell neoplasms, multiple myeloma and other; breast cancer and pregnancy; primary peritoneal cancer; prostate cancer; rectal cancer; renal cell cancer; transitional cell renal pelvis and ureter; salivary gland cancer; sarcoma, Kaposi; sarcoma, soft tissue, adult; sarcoma, uterine; mycosis fungoides and the sézary syndrome; skin cancer, melanoma; skin cancer, nonmelanoma; small cell lung cancer; small intestine cancer; stomach (gastric) cancer; testicular cancer; thymoma and thymic carcinoma; thyroid cancer; transitional cell cancer of the renal pelvis and ureter; trophoblastic disease, gestational; carcinoma of unknown primary; urethral cancer; uterine cancer, endometrial; uterine sarcoma; vaginal cancer; and vulvar cancer.

In some embodiments, non-limiting examples of cancer include, but are not limited to, hematologic and solid tumor types such as acoustic neuroma, acute leukemia, acute lymphoblastic leukemia, acute myelogenous leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer (including estrogen-receptor positive breast cancer), bronchogenic carcinoma, Burkitt's lymphoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, gastric carcinoma, germ cell testicular cancer, gestational trophobalstic disease, glioblastoma, head and neck cancer, heavy chain disease, hemangioblastoma, hepatoma, hepatocellular cancer, hormone insensitive prostate cancer, leiomyosarcoma, liposarcoma, lung cancer (including small cell lung cancer and non-small cell lung cancer), lymphangioendothelio-sarcoma, lymphangiosarcoma, lymphoblastic leukemia, lymphoma (lymphoma, including diffuse large B-cell lymphoma, follicular lymphoma, Hodgkin's lymphoma and non-Hodgkin's lymphoma), malignancies and hyPerproliferative disorders of the bladder, breast, colon, lung, ovaries, pancreas, prostate, skin and uterus, lymphoid malignancies of T-cell or B-cell origin, leukemia, medullary carcinoma, medulloblastoma, melanoma, meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, peripheral T-cell lymphoma, pinealoma, polycythemia vera, prostate cancer (including hormone-insensitive (refractory) prostate cancer), rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), stomach cancer, squamous cell carcinoma, synovioma, sweat gland carcinoma, testicular cancer (including germ cell testicular cancer), thyroid cancer, Waldenstrom's macroglobulinemia, testicular tumors, uterine cancer, Wilms' tumor and the like.

Non-limiting examples of the cancer include acute lymphoblastic leukemia, childhood; acute myeloid leukemia/other myeloid malignancies, childhood; adrenocortical carcinoma, childhood; astrocytomas, childhood; atypical teratoid/rhabdoid tumor, childhood central nervous system; basal cell carcinoma, childhood; bladder cancer, childhood; bone, malignant fibrous histiocytoma of and osteosarcoma; brain and spinal cord tumors overview, childhood; brain stem glioma, childhood; (brain tumor), childhood astrocytomas; (brain tumor), childhood central nervous system atypical teratoid/rhabdoid tumor; (brain tumor), childhood central nervous system embryonal tumors; (brain tumor), childhood central nervous system germ cell tumors; (brain tumor), childhood craniopharyngioma; (brain tumor), childhood ependymoma; breast cancer, childhood; bronchial tumors, childhood; carcinoid tumors, childhood; carcinoma of unknown primary, childhood; cardiac (heart) tumors, childhood; central nervous system atypical teratoid/rhabdoid tumor, childhood; central nervous system embryonal tumors, childhood; central nervous system germ cell tumors, childhood; cervical cancer, childhood; chordoma, childhood; colorectal cancer, childhood; craniopharyngioma, childhood; effects, treatment for childhood cancer, late; embryonal tumors, central nervous system, childhood;

ependymoma, childhood; esophageal tumors, childhood; esthesioneuroblastoma, childhood; ewing sarcoma; extracranial germ cell tumors, childhood; gastric (stomach) cancer, childhood; gastrointestinal stromal tumors, childhood; germ cell tumors, childhood central nervous system; germ cell tumors, childhood extracranial; glioma, childhood brain stem; head and neck cancer, childhood; heart tumors, childhood; hematopoietic cell transplantation, childhood; histiocytoma of bone, malignant fibrous and osteosarcoma; histiocytosis, langerhans cell; hodgkin lymphoma, childhood; kidney tumors of childhood, wilms tumor and other; langerhans cell histiocytosis; laryngeal cancer, childhood; late effects of treatment for childhood cancer; leukemia, childhood acute lymphoblastic; leukemia, childhood acute myeloid/other childhood myeloid malignancies; liver cancer, childhood; lung cancer, childhood; lymphoma, childhood Hodgkin; lymphoma, childhood non-Hodgkin; malignant fibrous histiocytoma of bone and osteosarcoma; melanoma, childhood; mesothelioma, childhood; midline tract carcinoma, childhood; multiple endocrine neoplasia, childhood; myeloid leukemia, childhood acute/other childhood myeloid malignancies; nasopharyngeal cancer, childhood; neuroblastoma, childhood; non-hodgkin lymphoma, childhood; oral cancer, childhood; osteosarcoma and malignant fibrous histiocytoma of bone; ovarian cancer, childhood; pancreatic cancer, childhood; papillomatosis, childhood; paraganglioma, childhood; pediatric supportive care; pheochromocytoma, childhood; pleuropulmonary blastoma, childhood; retinoblastoma; rhabdomyosarcoma, childhood; salivary gland cancer, childhood; sarcoma, childhood soft tissue; (sarcoma), ewing sarcoma; (sarcoma), osteosarcoma and malignant fibrous histiocytoma of bone; (sarcoma), childhood rhabdomyosarcoma; (sarcoma) childhood vascular tumors; skin cancer, childhood; spinal cord tumors overview, childhood brain and; squamous cell carcinoma (skin cancer), childhood; stomach (gastric) cancer, childhood; supportive care, pediatric; testicular cancer, childhood; thymoma and thymic carcinoma, childhood; thyroid tumors, childhood; transplantation, childhood hematopoietic; childhood carcinoma of unknown primary; unusual cancers of childhood; vaginal cancer, childhood; vascular tumors, childhood; and wilms tumor and other childhood kidney tumors.

Non-limiting examples of cancer include embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoid/rhabdoid tumor of the central nervous system, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer.

Methods for Preventing or Treating Autoimmune Diseases

Some embodiments disclosed herein provide methods for preventing an autoimmune disease in a human subject in need thereof, comprising identifying a human subject having an autoimmune disease and in need of an increased expression level of a gene associated with glutathione S-transferase; and administering to the human subject an effective amount of a nitroxide antioxidant. In some embodiments, the methods disclosed herein may be used to prevent the development of an autoimmune disease in a human subject showing no symptoms of an autoimmune disease, but is at risk of having an autoimmune disease. Exemplary risk factors for an autoimmune disease include, but are not limited to, age, family history, health conditions, medical history, habits, or a combination thereof. In some embodiments, risk factors for an autoimmune disease comprise a decreased expression level of one or more genes associated with glutathione S-transferase.

Autoimmunity is the system of immune responses of an organism against its own healthy cells and tissues. Any disease that results from such an aberrant immune response is termed an "autoimmune disease". Examples of autoimmune diseases include celiac disease, diabetes mellitus type 1, sarcoidosis, systemic lupus erythematosus (SLE), Sjögren's syndrome, eosinophilic granulomatosis with polyangiitis, Hashimoto's thyroiditis, Graves' disease, idiopathic thrombocytopenic purpura, Addison's disease, rheumatoid arthritis (RA), ankylosing spondylitis, polymyositis (PM), and dermatomyositis (DM). Autoimmune diseases are very often treated with steroids.

Toxicants, infections, epitope spreading, dysfunctions of immune homeostasis, and dietary components can all have an impact on the body's delicate immune recognition system. There may be common mechanisms in the immunopathogenesis of multiple autoimmune reactivities (Vojdani et al. A Potential Link between Environmental Triggers and Autoimmunity. Autoimmune Diseases (2014). dx.doi.org/10.1155/2014/437231; the content of which is incorporated herein in its entirety).

A number of clinical reports and experimental studies have shown that autoimmune responses and/or autoimmune diseases are induced in humans and laboratory animals by chronic exposure to various chemicals (Bigazzi. Autoimmunity caused by xenobiotics. Toxicology (1997) 119(1):1-21; the content of which is incorporated herein in its entirety). For example, the correlation between acetaminophen and primary biliary cirrhosis, the serologic hallmark of primary biliary cirrhosis (PBC) is the presence of antimitochondrial autoantibodies (AMAs) directed against the E2 subunit of the pyruvate dehydrogenase complex (PDC-E2). The PBC-related autoepitope of PDC-E2 contains lipoic acid, and it has been demonstrated that mimics of lipoic acid following immunization of mice lead to a PBC-like disease. Furthermore, approximately one-third of patients who have ingested excessive amounts of acetaminophen (paracetamol) develop AMA of the same specificity as patients with PBC. Quantitative structure-activity relationship (QSAR) data indicates that acetaminophen metabolites are particularly immunoreactive with AMA, and in genetically susceptible hosts, electrophilic modification of lipoic acid in PDC-E2 by acetaminophen or similar drugs can facilitate a loss of tolerance and lead to the development of PBC (Leung et al. Xenobiotics and autoimmunity: does acetaminophen cause primary biliary cirrhosis? Trends in Molecular Medicine. 18(10): 577-582; the content of which is incorporated herein in its entirety). Another example involves the development of hepatitis and associated environmental factors resulting in the development thereof. Exposure to certain xenobiotics such as trichloroethylene may disrupt certain mechanisms and promote autoimmune hepatitis (Gilbert, K., Xenobiotic Exposure and Autoimmune Hepatitis. Hepatitis Research and Treatment. (2010). dx.doi.org/10.1155/2010/248157; the content of which is incorporated herein in its entirety). Therefore, the regulation and increase of GST activity and the corresponding increase in glutathione activity in removing or neutralizing xenobiotics, by administration of a nitroxide antioxidant, prevents autoimmune disease.

T-helper 17 (Th17) cells, a unique CD4+ T-cell subset characterized by production of interleukin-17 (IL-17) are involved in human diseases. IL-17 is a highly inflammatory cytokine with robust effects on stromal cells in many tissues. Recent data in humans and mice suggest that Th17 cells play an important role in the pathogenesis of a diverse group of immune-mediated diseases, including psoriasis, rheumatoid arthritis, multiple sclerosis, inflammatory bowel disease, and asthma. Initial reports also propose a role for Th17 cells in tumorigenesis and transplant rejection. Important differences, as well as many similarities, are emerging when the biology of Th17 cells in the mouse is compared with corresponding phenomena in humans. As the understanding of human Th17 biology grows, the mechanisms underlying many diseases are becoming more apparent, resulting in a new appreciation for both previously known and more recently discovered cytokines, chemokines, and feedback mechanisms. Given the strong association between excessive Th17 activity and human disease, new therapeutic approaches targeting Th17 cells are highly promising, but the potential safety of such treatments may be limited by the role of these cells in normal host defenses against infection.

In some embodiments, the autoimmune disease is a manifestation of unregulated pathogenic activity of helper T-cells, mediated by one or more effector molecules. Helper T-cells are those differentiated from native CD4+ and classified in one or more subsets. Upon antigenic stimulation, naïve CD4+ T cells activate, expand and differentiate into different effector phenotypes. TH17 cells, which have been characterized as an additional effector T cell subset that produce interleukin (IL) glycoproteins IL-17A, IL-17F, IL-21 and IL-22, are known to be the critical driver of autoimmune tissue inflammation TH17 has been identified as having non-pathogenic and pathogenic function in the presence of effector cells or effector molecules IL-1 beta, IL-6, and IL-23.

In some embodiments, administering to the human subject an effective amount of the nitroxide antioxidant results in an increased expression level of a gene, for example a gene associated with glutathione S-transferase. The gene associated with glutathione S-transferase can be Gstm3, Gstm6, Gsta3, Gstt1, Gsta4, Gstm1, Gstm4, Gstt2, Gstp1, or Gstk1. The treatment of the human subject with the effective amount of the nitroxide antioxidant can result in an increased expression level of the gene. For example, the treatment can result in increased expression levels of Gstm3, Gstm6, Gsta3, Gstt1, Gsta4, Gstm1, Gstm4, Gstt2, Gstp1, Gstk1, or any combination thereof. The increased expression levels of Gstm3, Gstm6, Gsta3, Gstt1, Gsta4, Gstm1, Gstm4, Gstt2, Gstp1, Gstk1, or any combination thereof, can increase the level of apoptosis. The increased level of apoptosis can result in a decrease in or disappearance of signs and symptoms of the autoimmune disease, including the curing of the autoimmune disease. In some embodiments, the increased expression levels of Gstm3, Gstm6, Gsta3, Gstt1, Gsta4, Gstm1, Gstm4, Gstt2, Gstp1, Gstk1, or any combination thereof, can decrease the level of apoptosis. The decreased level of apoptosis can result in a decrease in or disappearance of signs and symptoms of the autoimmune disease, including the prevention of the autoimmune disease development.

Some embodiments disclosed herein provide methods for treating an autoimmune disease in a human subject in need thereof, comprising identifying a human subject having an autoimmune disease and in need of an increased expression level of a gene associated with glutathione S-transferase; and administering to the human subject an effective amount of a nitroxide antioxidant. In some embodiments, the methods disclosed herein may be used to treat a human subject shows no symptoms of an autoimmune disease, but is at risk of having an autoimmune disease. Exemplary risk factors for an autoimmune disease include, but are not limited to, age, family history, health conditions, medical history, habits, or a combination thereof. In some embodiments, risk factors for an autoimmune disease comprise a decreased expression level of one or more genes associated with glutathione S-transferase.

In some embodiments, administering to the human subject an effective amount of the nitroxide antioxidant results in an increased expression level of a gene, for example a gene associated with glutathione S-transferase. The gene associated with glutathione S-transferase can be Gstm3, Gstm6, Gsta3, Gstt1, Gsta4, Gstm1, Gstm4, Gstt2, Gstp1, or Gstk1. The treatment of the human subject with the effective amount of the nitroxide antioxidant can result in an increased expression level of the gene. For example, the treatment can result in increased expression levels of Gstm3, Gstm6, Gsta3, Gstt1, Gsta4, Gstm1, Gstm4, Gstt2, Gstp1, Gstk1, or any combination thereof. The increased expression levels of Gstm3, Gstm6, Gsta3, Gstt1, Gsta4, Gstm1, Gstm4, Gstt2, Gstp1, Gstk1, or any combination thereof, can increase the level of apoptosis. The increased level of apoptosis can result in a decrease in or disappearance of signs and symptoms of the autoimmune disease, including the curing of the autoimmune disease. In some embodiments, the increased expression levels of Gstm3, Gstm6, Gsta3, Gstt1, Gsta4, Gstm1, Gstm4, Gstt2, Gstp1, Gstk1, or any combination thereof, can decrease the level of apoptosis. The decreased level of apoptosis can result in a decrease in or disappearance of signs and symptoms of the autoimmune disease, including the curing of the autoimmune disease.

Non-limiting examples of autoimmune diseases include rheumatoid arthritis, osteoarthritis, juvenile chronic arthritis, septic arthritis, Lyme arthritis, psoriatic arthritis, reactive arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis scleroderma, graft versus host disease, organ transplant rejection, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpurea, microscopic vasculitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, Alzheimer's disease, stroke, primary biliary cirrhosis, hemolytic anemia, malignancies, heart failure, myocardial infarction, Addison's disease, sporadic, polyglandular deficiency type I and polyglandular deficiency type II, Schmidt's syndrome, adult (acute) respiratory distress syndrome, alopecia, alopecia greata, seronegative arthopathy, arthropathy, Reiter's disease, psoriatic arthropathy, ulcerative colitic arthropathy, enteropathic synovitis, chlamydia, *Yersinia* and *Salmonella* associated arthropathy, spondyloarthopathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis B, Hepatitis C, common varied immunodeficiency (common variable hypogammaglobulinaemia), dilated cardiomyopathy, female infertility, ovarian failure, premature ovarian failure, fibrotic lung disease, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjogren's disease associated lung disease, ankylosing spondylitis associated lung disease, vasculitic diffuse lung disease, haemosiderosis associated lung disease, drug-induced interstitial lung disease, fibrosis, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropaenia, renal disease NOS, glomerulonephritides, microscopic vasulitis of the kidneys, lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Sjogren's syndrome, Takayasu's disease/arteritis, autoimmune thrombocytopaenia, idiopathic thrombocytopaenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo acute liver disease, chronic liver diseases, alcoholic cirrhosis, alcohol-induced liver injury, choleosatatis, idiosyncratic liver disease, Drug-Induced hepatitis, Non-alcoholic Steatohepatitis, allergy and asthma, group B streptococci (GB S) infection, mental disorders (e.g., depression and schizophrenia), Th2 Type and Th1 Type mediated diseases, acute and chronic pain (different forms of pain), and cancers such as lung, breast, stomach, bladder, colon, pancreas, ovarian, prostate and rectal cancer and hematopoietic malignancies (leukemia and lymphoma). The human antibodies, and antibody portions of the present application can be used to treat humans suffering from autoimmune diseases, in particular those associated with inflammation, including, rheumatoid spondylitis, allergy, autoimmune diabetes, autoimmune uveitis.

Non-limiting examples of autoimmune diseases include acquired immunodeficiency disease syndrome (AIDS), autoimmune lymphoproliferative syndrome, hemolytic anemia, inflammatory diseases, and thrombocytopenia, acute or chronic immune disease associated with organ transplantation, Addison's disease, allergic diseases, alopecia, alopecia areata, atheromatous disease/arteriosclerosis, atherosclerosis, arthritis (including osteoarthritis, juvenile chronic arthritis, septic arthritis, Lyme arthritis, psoriatic arthritis and reactive arthritis), autoimmune bullous disease, abetalipoprotemia, acquired immunodeficiency-related diseases, acute immune disease associated with organ transplantation, acquired acrocyanosis, acute and chronic parasitic or infectious processes, acute pancreatitis, acute renal failure, acute rheumatic fever, acute transverse myelitis, adenocarcinomas, aerial ectopic beats, adult (acute) respiratory distress syndrome, AIDS dementia complex, alcoholic cirrhosis, alcohol-induced liver injury, alcohol-induced hepatitis, allergic conjunctivitis, allergic contact dermatitis, allergic rhinitis, allergy and asthma, allograft rejection, alpha-1-antitrypsin deficiency, Alzheimer's disease, amyotrophic lateral sclerosis, anemia, angina pectoris, ankylosing spondylitis associated lung disease, anterior horn cell degeneration, antibody mediated cytotoxicity, antiphospholipid syndrome, anti-receptor hypersensitivity reactions, aortic and peripheral aneurysms, aortic dissection, arterial hypertension, arteriosclerosis, arteriovenous fistula, arthropathy, asthenia, asthma, ataxia, atopic allergy, atrial fibrillation (sustained or paroxysmal), atrial flutter, atrioventricular block, atrophic autoimmune hypothyroidism, autoimmune haemolytic anaemia, autoimmune hepatitis, type-1 autoimmune hepatitis (classical autoimmune or lupoid hepatitis), autoimmune mediated hypoglycaemia, autoimmune neutropaenia, autoimmune thrombocytopaenia, autoimmune thyroid disease, B cell lymphoma, bone graft rejection, bone marrow transplant (BMT) rejection, bronchiolitis obliterans, bundle branch block, burns, cachexia, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chlamydia, choleosatatis, chronic alcoholism, chronic active hepatitis, chronic fatigue syndrome, chronic immune disease associated with organ transplantation, chronic eosinophilic pneumonia, chronic inflammatory pathologies, chronic mucocutaneous candidiasis, chronic obstructive pulmonary disease (COPD), chronic salicylate intoxication, colorectal common varied immunodeficiency (common variable hypogammaglobulinaemia), conjunctivitis, connective tissue disease associated interstitial lung disease, contact dermatitis, Coombs positive haemolytic anaemia, cor pulmonale, Creutzfeldt-Jakob disease, cryptogenic autoimmune hepatitis, cryptogenic fibrosing alveolitis, culture negative sepsis, cystic fibrosis, cytokine therapy associated disorders, Crohn's disease, dementia pugilistica, demyelinating diseases, dengue hemorrhagic fever, dermatitis, dermatitis scleroderma, dermatologic conditions, dermatomyositis/polymyositis associated lung disease, diabetes, diabetic arteriosclerotic disease, diabetes mellitus, Diffuse Lewy body disease, dilated cardiomyopathy, dilated congestive cardiomyopathy, discoid lupus erythematosus, disorders of the basal ganglia, disseminated intravascular coagulation, Down's Syndrome in middle age, drug-induced interstitial lung disease, drug-induced hepatitis, drug-induced movement disorders induced by drugs which block CNS dopamine, receptors, drug sensitivity, eczema, encephalomyelitis, endocarditis, endocrinopathy, enteropathic synovitis, epiglottitis, Epstein-Barr virus infection, erythromelalgia, extrapyramidal and cerebellar disorders, familial hematophagocytic lymphohistiocytosis, fetal thymus implant rejection, Friedreich's ataxia, functional peripheral arterial disorders, female infertility, fibrosis, fibrotic lung disease, fungal sepsis, gas gangrene, gastric ulcer, giant cell arteritis, glomerular nephritis, glomerulonephritides, Goodpasture's syndrome, goitrous autoimmune hypothyroidism (Hashimoto's disease), gouty arthritis, graft rejection of any organ or tissue, graft versus host disease, gram negative sepsis, gram positive sepsis, granulomas due to intracellular organisms, group B streptococci (GBS) infection, Grave's disease, haemosiderosis associated lung disease, hairy cell leukemia, hairy cell leukemia, Hallerrorden-Spatz disease, Hashimoto's thyroiditis, hay fever, heart transplant rejection, hemachromatosis, hematopoietic malignancies (leukemia and lymphoma), hemolytic anemia, hemolytic uremic syndrome/thrombolytic thrombocytopenic purpura, hemorrhage, Henoch-Schoenlein purpurea, Hepatitis A, Hepatitis B, Hepatitis C, HIV infection/HIV neuropathy, Hodgkin's disease, hypoparathyroidism, Huntington's chorea, hyperkinetic movement disorders, hypersensitivity reactions, hypersensitivity pneumonitis, hyperthyroidism, hypokinetic movement disorders, hypothalamic-pituitary-adrenal axis evaluation, idiopathic Addison's disease, idiopathic leucopaenia, idiopathic pulmonary fibrosis, idiopathic thrombocytopaenia, idiosyncratic liver disease, infantile spinal muscular atrophy, infectious diseases, inflammation of the aorta, inflammatory bowel disease, insulin dependent diabetes mellitus, interstitial pneumonitis, iridocyclitis/uveitis/optic neuritis, ischemia-reperfusion injury, ischemic stroke, juvenile pernicious anaemia, juvenile rheumatoid arthritis, juvenile spinal muscular atrophy, Kaposi's sarcoma, Kawasaki's disease, kidney transplant rejection, legionella, leishmaniasis, leprosy, lesions of the corticospinal system, linear IgA disease, lipidema, liver transplant rejection, Lyme disease, lymphederma, lymphocytic infiltrative lung disease, malaria, male infertility idiopathic or NOS, malignant histiocytosis, malignant melanoma, meningitis, meningococcemia, microscopic vasculitis of the kidneys, migraine headache, mitochondrial multisystem disorder, mixed connective tissue disease, mixed connective tissue disease associated lung disease, monoclonal gammopathy, multiple myeloma, multiple systems degenerations (Mencel Dejerine-Thomas Shi-Drager and Machado-Joseph), myalgic encephalitis/Royal Free Disease, myasthenia gravis, microscopic vasculitis of the kidneys, *Mycobacterium avium* intracellulare, *Mycobacterium tuberculosis*, myelodyplastic syndrome, myocardial infarction, myocardial ischemic disorders, nasopharyngeal carcinoma, neonatal chronic lung disease, nephritis, nephrosis, nephrotic syndrome, neurodegenerative diseases, neurogenic I muscular atrophies, neutropenic fever, Non-alcoholic Steatohepatitis, occlusion of the abdominal aorta and its branches, occlusive arterial disorders, organ transplant rejection, orchitis/epidydimitis, orchitis/vasectomy reversal procedures, organomegaly, osteoarthrosis, osteoporosis, ovarian failure, pancreas transplant rejection, parasitic diseases, parathyroid transplant rejection, Parkinson's disease, pelvic inflammatory disease, pemphigus vulgaris, pemphigus foliaceus, pemphigoid, perennial rhinitis, pericardial disease, peripheral atherlosclerotic disease, peripheral vascular disorders, peritonitis, pernicious anemia, phacogenic uveitis, *Pneumocystis carinii* pneumonia, pneumonia, POEMS syndrome (polyneuropathy, organomegaly, endocrinopathy, monoclonal gammopathy, and skin changes syndrome), post perfusion syndrome, post pump syndrome, post-MI cardiotomy syndrome, postinfectious interstitial lung disease, premature ovarian failure, primary biliary cirrhosis, primary sclerosing hepatitis, primary myxoedema, primary pulmonary hypertension, primary sclerosing cholangitis, primary vasculitis, Progressive supranucleo Palsy, psoriasis, psoriasis type 1, psoriasis type 2, psoriatic arthropathy, pulmonary hypertension secondary to connective tissue disease, pulmonary manifestation of polyarteritis nodosa, post-inflammatory interstitial lung disease, radiation fibrosis, radiation therapy, Raynaud's phenomenon and disease, Raynoud's disease, Refsum's disease, regular narrow QRS tachycardia, Reiter's disease, renal disease NOS, renovascular hypertension, reperfusion injury, restrictive cardiomyopathy, rheumatoid arthritis associated interstitial lung disease, rheumatoid spondylitis, sarcoidosis, Schmidt's syndrome, scleroderma, senile chorea, Senile Dementia of Lewy body type, sepsis syndrome, septic shock, seronegative arthropathies, shock, sickle cell anemia, Sjögren's disease associated lung disease, Sjörgren's syndrome, skin allograft rejection, skin changes syndrome, small bowel transplant rejection, sperm autoimmunity, multiple sclerosis (all subtypes), spinal ataxia, spinocerebellar degenerations, spondyloarthropathy, spondyloarthopathy, sporadic, polyglandular deficiency type I sporadic, polyglandular deficiency type II, Still's disease, streptococcal myositis, stroke, structural lesions of the cerebellum, Subacute sclerosing panencephalitis, sympathetic ophthalmia, Syncope, syphilis of the cardiovascular system, systemic anaphylaxis, systemic inflammatory response syndrome, systemic onset juvenile rheumatoid arthritis, systemic lupus erythematosus, systemic lupus erythematosus-associated lung disease, systemic sclerosis, systemic sclerosis-associated interstitial lung disease, T-cell or FAB ALL, Takayasu's disease/arteritis, Telangiectasia, Th2 Type and Th1 Type mediated diseases, thromboangitis obliterans, thrombocytopenia, thyroiditis, toxicity, toxic shock syndrome, transplants, trauma/hemorrhage, type-2 autoimmune hepatitis (anti-LKM antibody hepatitis), type B insulin resistance with acanthosis nigricans, type III hypersensitivity reactions, type IV hypersensitivity, ulcerative colitic arthropathy, ulcerative colitis, unstable angina, uremia, urosepsis, urticaria, uveitis, valvular heart diseases, varicose veins, vasculitis, vasculitic diffuse lung disease, venous diseases, venous thrombosis, ventricular fibrillation, vitiligo acute liver disease, viral and fungal infections, vital encephalitis/aseptic meningitis, vital-associated hemaphagocytic syndrome, Wegener's granulomatosis, Wernicke-Korsakoff syndrome, Wilson's disease, xenograft rejection of any organ or tissue, *Yersinia* and *Salmonella*-associated arthropathy and the like.

Nitroxide Antioxidant

Non-limiting examples of the nitroxide antioxidant include 2-ethyl-2,5,5-trimethyl-3-oxazolidine-1-oxyl (OXANO), 2,2,6,6-tetramethylpiperidine-1-oxyl (TEMPO), 4-hydroxy-2,2,6,6-tetramethylpiperidine-1-oxyl (TEMPOL), 4-amino-2,2,6,6-tetramethyl-1-piperidinyloxy (Tempamine), 3-Aminomethyl-PROXYL, 3-Cyano-PROXYL, 3-Carbamoyl-PROXYL, 3-Carboxy-PROXYL, and 4-Oxo-TEMPO. TEMPO can also be substituted, typically in the 4 position, for example, 4-amino, 4-(2-bromoacetamido), 4-(ethoxyfluorophosphonyloxy), 4-hydroxy, 4-(2-iodoacetamido), 4-isothiocyanato, 4-maleimido, 4-(4-nitrobenzoyloxy), 4-phosphonooxy, and the like.

The use of other nitroxide compounds is also contemplated. According to certain embodiments the nitroxide compound can be selected from the following formulas:

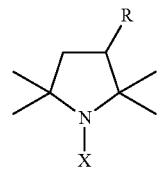

wherein X is selected from O— and OH, and R is selected from COOH, CONH, CN, and CH2NH2;

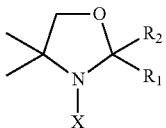

wherein X is selected from O— and OH, and R1 is selected from CH3 and spirocyclohexyl, and R2 is selected from C2H5 and spirocyclohexyl;

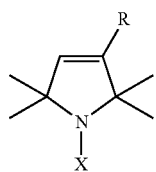

wherein X is selected from O— and OH and R is selected from CONH; and

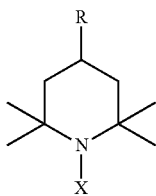

wherein X is selected from O— and OH and R is selected from H, OH, and NH2.

Suitable nitroxide compounds can also be found in Proctor, U.S. Pat. No. 5,352,442, and Mitchell et al., U.S. Pat. No. 5,462,946, both of which are hereby incorporated by reference in their entireties.

In some embodiments, the nitroxide antioxidant includes or is associated with (e.g., binds to or is conjugated with) a bioeffector molecule. For example, the bioeffector molecule is a targeting subunit bound to the nitroxide antioxidant, such as a mitochondrial targeting subunit. A targeting subunit candirect activity of the nitroxide antioxidant to a predetermined location within or on the cell. Non-limiting examples of mitochondrial targeting bioeffector molecules includes triphenylphosphine (TPP), gramicidin, and any functional group effectively charged to be attracted to the polarized mitochondria.

In some embodiments, the nitroxide antioxidant is structurally cyclic having a ring structure including a nitroxide molecule incorporated therein. In some embodiments, the nitroxide antioxidant is characterized as the nitroxide molecule functioning as the catalytic center.

Dosage

In some embodiments, the nitroxide antioxidant, non-toxic salts thereof, acid addition salts thereof or hydrates thereof may be administered systemically or locally, usually by oral or parenteral administration. The doses to be administered can be determined depending upon, for example, age, body weight, symptom, the desired therapeutic effect, the route of administration, and the duration of the treatment. In the human adult, the dose per person at a time can be generally from about 0.01 to about 1000 mg, by oral administration, up to several times per day. Specific examples of particular amounts contemplated via oral administration include about 0.02, 0.03, 0.04, 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, 1000 or more mg. The dose per person at a time can be generally from about 0.01 to about 300 mg/kg via parenteral administration (preferably intravenous administration), from one to four or more times per day. Specific examples of particular amounts contemplated include about 0.02, 0.03, 0.04, 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1, 2, 3, 4, 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300 or more mg/kg. Continuous intravenous administration can also contemplated for from 1 to 24 hours per day to achieve a target concentration from about 0.01 mg/L to about 100 mg/L. Non-limiting examples of particular amounts contemplated via this route include about 0.02, 0.03, 0.04, 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more mg/L. The dose to be used does can depend upon various conditions, and there may be cases wherein doses lower than or greater than the ranges specified above are used.

Compositions

The nitroxide antioxidant can be administered in the form of, for example, solid compositions, liquid compositions or other compositions for oral administration, injections, liniments or suppositories for parenteral administration.

Solid compositions for oral administration include compressed tablets, pills, capsules, dispersible powders and granules. Capsules include hard capsules and soft capsules. In such solid compositions, Tempol may be admixed with an excipient (e.g. lactose, mannitol, glucose, microcrystalline cellulose, starch), combining agents (hydroxypropyl cellulose, polyvinyl pyrrolidone or magnesium metasilicate aluminate), disintegrating agents (e.g. cellulose calcium glycolate), lubricating agents (e.g. magnesium stearate), stabilizing agents, agents to assist dissolution (e.g. glutamic acid or aspartic acid), or the like. The agents may, if desired, be coated with coating agents (e.g. sugar, gelatin, hydroxypropyl cellulose or hydroxypropylmethyl cellulose phthalate), or be coated with two or more films. Further, coating may include containment within capsules of absorbable materials such as gelatin.

Liquid compositions for oral administration include pharmaceutically acceptable solutions, suspensions, emulsions, syrups and elixirs. In such compositions, the nitroxide antioxidant is dissolved, suspended or emulsified in a commonly used diluent (e.g. purified water, ethanol or mixture thereof). Furthermore, such liquid compositions may also comprise wetting agents or suspending agents, emulsifying agents, sweetening agents, flavoring agents, perfuming agents, preserving agents, buffer agents, or the like.

Injections for parenteral administration include solutions, suspensions, emulsions and solids which are dissolved or suspended. For injections, the nitroxide antioxidant can be dissolved, suspended and emulsified in a solvent. The solvents include, for example, distilled water for injection, physiological salt solution, vegetable oil, propylene glycol, polyethylene glycol, alcohol such as ethanol, or a mixture thereof. Moreover the injections can also include stabilizing agents, agents to assist dissolution (e.g. glutamic acid, aspartic acid or POLYSORBATE80™), suspending agents, emulsifying agents, soothing agents, buffer agents, preserving agents, etc. They can be sterilized in the final process or manufactured and prepared by sterile procedure. They can also be manufactured in the form of sterile solid compositions, such as a freeze-dried composition, and they may be sterilized or dissolved immediately before use in sterile distilled water for injection or some other solvent.

Other compositions for parenteral administration include liquids for external use, and ointment, endermic liniments, inhale, spray, suppositories for rectal administration and pessaries for vaginal administration which comprise the nixtroxide antioxidant and are administered by methods known in the art.

Spray compositions can comprise additional substances other than diluents: e.g. stabilizing agents (e.g. sodium sulfite hydride), isotonic buffers (e.g. sodium chloride, sodium citrate or citric acid). A small aerosol particle size useful for effective distribution of the medicament can be obtained by employing self-propelling compositions containing the drugs in micronized form dispersed in a propellant composition. Effective dispersion of the finely divided drug particles can be accomplished with the use of very small quantities of a suspending agent, present as a coating on the micronized drug particles. Evaporation of the propellant from the aerosol particles after spraying from the aerosol container leaves finely divided drug particles coated with a fine film of the suspending agent. In the micronized form, the average particle size can be less than about 5 microns. The propellant composition may employ, as the suspending agent, a fatty alcohol such as oleyl alcohol. The minimum quantity of suspending agent can be approximately 0.1 to 0.2 percent by weight of the total composition. The amount of suspending agent can be less than about 4 percent by weight of the total composition to maintain an upper particle size limit of less than 10 microns or 5 microns. Propellants that may be employed include hydrofluoroalkane propellants and chlorofluorocarbon propellants. Dry powder inhalation may also be employed.

EXAMPLES

Some aspects of the embodiments discussed above are disclosed in further detail in the following examples, which are not in any way intended to limit the scope of the present disclosure.

In order to facilitate understanding, the specific embodiments are provided to help interpret the technical proposal, that is, these embodiments are only for illustrative purposes, but not in any way to limit the scope of the invention. Unless otherwise specified, embodiments do not indicate the specific conditions, are in accordance with the conventional conditions or the manufacturer's recommended conditions.

Example 1. Effects of Tempol on Expression of Genes Associated with Glutathione S-Transferase To assess the effects of Tempol on gene expression, Tempol was administered to experimental mice at a dose of 5 mg/g of food from 14 months to 31 months after birth. Mice receiving the same food without the addition of Tempol were used as a negative control. At the age of 31 months, the experimental animals were sacrificed and the hearts were surgically removed. The expression of a broad spectrum of genes in white adipose tissue tissue was assessed using chip-based microarray technology. Such chips are well known in the art and are widely used to assess gene expression. The experimental results showed that ten genes associated with glutathione S-transferase, Gstm3, Gstm6, Gsta3, Gstt1, Gsta4, Gstm1, Gstm4, Gstt2, Gstp1, and Gstk1, exhibited statistically significant increase in expression. This result is shown in Table 1.

TABLE 1

Genes associated with Glutathione S-Transferase exhibited increased expression in white adipose tissue after Tempol administration.

| Gene | Control mice | Tempol-treated mice | Fold change | P-value |
| --- | --- | --- | --- | --- |
| Glutathione S-transferase, mu 3 (Gstm3) | 10 | 74 | 7.52 | 0.001 |
| Glutathione S-transferase, mu 6 (Gstm6) | 147 | 265 | 1.8 | 0.034 |
| Glutathione S-transferase, alpha 3 (Gsta3) | 668 | 1183 | 1.77 | 0.004 |
| Glutathione S-transferase, theta 1 (Gstt1) | 1017 | 1619 | 1.59 | 0.001 |
| Glutathione S-transferase, alpha 4 (Gsta4) | 195 | 284 | 1.45 | 0.006 |
| Glutathione S-transferase, mu 1 (Gstm1) | 6291 | 8548 | 1.36 | 0.003 |
| Glutathione S-transferase, mu 4 (Gstm4) | 416 | 533 | 1.28 | 0.003 |
| Glutathione S-transferase, theta 2 (Gstt2) | 446 | 546 | 1.22 | 0.035 |
| Glutathione S-transferase, pi 1 (Gstp1) | 5711 | 6812 | 1.19 | 0.005 |
| Glutathione S-transferase kappa1 (Gstk1) | 1140 | 1325 | 1.16 | 0.015 |

Example 2. Treating Age-Related Decrease in Gene Expression

A 70-kilogram human subject over the age of 65 is identified for decreased expression level of Gstm3, Gstm6, Gsta3, Gstt1, Gsta4, Gstm1, Gstm4, Gstt2, Gstp1, or Gstk1. The human subject is administered a dose of 1500 mg of a nitroxide antioxidant (e.g., Tempol) per day for 180 days. This may be administered in a single dose, or may be administered as a number of smaller doses over a 24-hour period: for example, three 500-mg doses at eight-hour intervals. Following treatment, the serum level of Gstm3, Gstm6, Gsta3, Gstt1, Gsta4, Gstm1, Gstm4, Gstt2, Gstp1, or Gstk1, is increased.

Example 3. Treating a Human Subject with Age-Related Disease

A 70-kilogram human subject over the age of 65 and having a cardiovascular disease is identified for decreased expression level of Gstm3, Gstm6, Gsta3, Gstt1, Gsta4, Gstm1, Gstm4, Gstt2, Gstp1, or Gstk1. The human subject is administered a dose of 1500 mg of a nitroxide antioxidant (e.g., Tempol) per day for 180 days. This may be administered in a single dose, or may be administered as a number of smaller doses over a 24-hour period: for example, three 500-mg doses at eight-hour intervals. Following treatment, the serum level of Gstm3, Gstm6, Gsta3, Gstt1, Gsta4, Gstm1, Gstm4, Gstt2, Gstp1, or Gstk1, is increased.

Example 4. Treating a Human Subject with Decreased Gene Expression

A 70-kilogram human subject is identified for decreased expression level of Gstm3, Gstm6, Gsta3, Gstt1, Gsta4, Gstm1, Gstm4, Gstt2, Gstp1, or Gstk1. The human subject is administered a dose of 1500 mg of a nitroxide antioxidant (e.g., Tempol) per day for 180 days. This may be administered in a single dose, or may be administered as a number of smaller doses over a 24-hour period: for example, three 500-mg doses at eight-hour intervals. Following treatment, the serum level of Gstm3, Gstm6, Gsta3, Gstt1, Gsta4, Gstm1, Gstm4, Gstt2, Gstp1, or Gstk1, is increased.

Example 5. Treating a Human Subject with Decreased Gene Expression Associated with a Disease A 70-kilogram human subject is identified for decreased expression level of Gstm3, Gstm6, Gsta3, Gstt1, Gsta4, Gstm1, Gstm4, Gstt2, Gstp1, or Gstk1 that is associated with a disease (e.g., caused by or causing a disease). The human subject is administered a dose of 1500 mg of a nitroxide antioxidant (e.g., Tempol) per day for 180 days. This may be administered in a single dose, or may be administered as a number of smaller doses over a 24-hour period: for example, three 500-mg doses at eight-hour intervals. Following treatment, the serum level of Gstm3, Gstm6, Gsta3, Gstt1, Gsta4, Gstm1, Gstm4, Gstt2, Gstp1, or Gstk1, is increased.

Example 6. Treating a Human Subject at Risk of Developing Cancer or Having a Cancer A 70-kilogram human subject at risk of developing a cancer (e.g., colorectal cancer) or having a cancer is identified for decreased expression level of Gstm3, Gstm6, Gsta3, Gstt1, Gsta4, Gstm1, Gstm4, Gstt2, Gstp1, or Gstk1. The human subject is administered a dose of 1500 mg of a nitroxide antioxidant (e.g., Tempol) per day for 180 days. This may be administered in a single dose, or may be administered as a number of smaller doses over a 24-hour period: for example, three 500-mg doses at eight-hour intervals. Following treatment, the serum level of Gstm3, Gstm6, Gsta3, Gstt1, Gsta4, Gstm1, Gstm4, Gstt2, Gstp1, or Gstk1, is increased.

Example 7. Treating a Human Subject at Risk of Developing an Autoimmune Disease or Having an Autoimmune Disease A 70-kilogram human subject at risk of developing or having an autoimmune disease (e.g., rheumatoid arthritis) is identified for decreased expression level of Gstm3, Gstm6, Gsta3, Gstt1, Gsta4, Gstm1, Gstm4, Gstt2, Gstp1, or Gstk1. The human subject is administered a dose of 1500 mg of a nitroxide antioxidant (e.g., Tempol) per day for 180 days. This may be administered in a single dose, or may be administered as a number of smaller doses over a 24-hour period: for example, three 500-mg doses at eight-hour intervals. Following treatment, the serum level of Gstm3, Gstm6, Gsta3, Gstt1, Gsta4, Gstm1, Gstm4, Gstt2, Gstp1, or Gstk1, is increased.

Example 8. Treating a Human Subject at Risk of Developing, or Having, a Condition Due to Aging A 70-kilogram human subject of 45 years old at risk of developing, or having, a condition due to aging is identified. The human subject is administered a dose of 1500 mg of a nitroxide antioxidant (e.g., Tempol) per day for 180 days. This may be administered in a single dose, or may be administered as a number of smaller doses over a 24-hour period: for example, three 500-mg doses at eight-hour intervals. Following treatment, the serum level of Gstm3, Gstm6, Gsta3, Gstt1,Gsta4, Gstm1, Gstm4, Gstt2, Gstp1, or Gstk1, is increased.

Example 9. Treating a Human Subject at Risk of Developing, or Having, a Neruodegenerative Disease A 70-kilogram human subject at risk of developing, or having, a neurodegenerative disease (e.g., Parkinson's Disease) is identified for decreased expression level of Gstm3, Gstm6, Gsta3, Gstt1, Gsta4, Gstm1, Gstm4, Gstt2, Gstp1, or Gstk1. Or a 70-kilogram human subject is known to be at risk of developing a neurodegenerative disease and/or have increased expression level of Gstm3, Gstm6, Gsta3, Gstt1, Gsta4, Gstm1, Gstm4, Gstt2, Gstp1, or Gstk1. The human subject is administered a dose of 1500 mg of Tempol (or another nitroxide antioxidant) per day for 180 days. This may be administered in a single dose, or may be administered as a number of smaller doses over a 24-hour period: for example, three 500-mg doses at eight-hour intervals. Following treatment, the serum level of Gstm3, Gstm6, Gsta3, Gstt1, Gsta4, Gstm1, Gstm4, Gstt2, Gstp1, or Gstk1, is increased.

Example 10. Treating a Human Subject Having an Infection

A 70-kilogram human subject having an infection (e.g., a bacterial, fungal, or viral infection) is identified for decreased expression level of Gstm3, Gstm6, Gsta3, Gstt1, Gsta4, Gstm1, Gstm4, Gstt2, Gstp1, or Gstk1. Or a 70-kilogram human subject is known to have an infection and/or have decreased expression level of Gstm3, Gstm6, Gsta3, Gstt1, Gsta4, Gstm1, Gstm4, Gstt2, Gstp1, or Gstk1. The human subject is administered a dose of 1500 mg of Tempol (or another nitroxide antioxidant) per day for 180 days. This may be administered in a single dose, or may be administered as a number of smaller doses over a 24-hour period: for example, three 500-mg doses at eight-hour intervals. Following treatment, the serum level of Gstm3, Gstm6, Gsta3, Gstt1, Gsta4, Gstm1, Gstm4, Gstt2, Gstp1, or Gstk1, is increased.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of upregulating an expression level of one or more glutathione S-transferase (GST) genes, the method comprising:

administering an effective amount of a nitroxide antioxidant to an individual known to have or suspected to have oxidative stress, whereby the expression level of the GST gene is upregulated, the oxidative stress caused by a disease or condition selected from the group consisting of cancer, rheumatoid/osteoid arthritis, systemic lupus erythematosus (SLE), inflammatory bowel disease, Alzheimer's disease, multiple sclerosis, atherosclerosis, cardiovascular disease, cataracts, dementia, osteoporosis, type 2 diabetes, chemotherapy, radiation therapy and hypertension, and the nitroxide antioxidant selected from the group consisting of 2-ethyl-2,5,5-trimethyl-3-oxazolidine-1-oxyl (OXANO), 2,2,6,6-tetramethylpiperidine-1-oxyl (TEMPO), 4-hydroxy-2,2,6,6-tetramethylpiperidine-1-oxyl (TEMPOL), 4-amino-2,2,6,6-tetramethyl-1-piperidinyloxy (Tempamine), 3-Aminomethyl-PROXYL, 3-Cyano-PROXYL, 3-Carbamoyl-PROXYL, 3-Carboxy-PROXYL, 4-Oxo-TEMPO, 4-amino-TEMPO, 4-(2-bromoacetamido)-TEMPO, 4-ethoxyfluorophosphonyloxy-TEMPO, 4-hydroxy-TEMPO, 4-(2-iodoacetamido)-TEMPO, 4-isothiocyanato-TEMPO, 4-maleimido-TEMPO, 4-(4-nitrobenzoyloxyl)-TEMPO, or 4-phosphonooxy-TEMPO.

2. The method of claim 1, wherein the GST gene is selected from the group consisting of Gstm3, Gstm6, Gsta3, Gstt1, Gsta4, Gstm1, Gstm4, Gstt2, Gstp1, and Gstk1.

3. The method of claim 2, wherein the nitroxide antioxidant is 4-hydroxy-2,2,6,6-tetramethylpiperidine-1-oxyl (TEMPOL).

4. The method of claim 1, wherein the individual has been administered a chemotherapeutic agent.

5. The method of claim 1, wherein the nitroxide antioxidant is chemically attached to one or more bioeffector molecules.

6. The method of claim 1, further comprising administering to the individual a xenobiotic prior to administering to the individual the effective amount of the nitroxide antioxidant.

7. The method of claim 1, wherein the effective amount of the nitroxide antioxidant comprises about 5 mg/g of food.

8. The method of claim 1, wherein the effective amount of the nitroxide antioxidant comprises about 500-1500 mg/g.

9. The method of claim 3, wherein the oxidative stress caused by cancer.

10. The method of claim 3, wherein the oxidative stress caused by rheumatoid/osteoid arthritis.

11. The method of claim 3, wherein the oxidative stress caused by systemic lupus erythematosus (SLE).

12. The method of claim 3, wherein the oxidative stress caused by inflammatory bowel disease.

13. The method of claim 3, wherein the oxidative stress caused by Alzheimer's disease.

14. The method of claim 3, wherein the oxidative stress caused by multiple sclerosis.

15. The method of claim 3, wherein the oxidative stress caused by atherosclerosis.

16. The method of claim 3, wherein the oxidative stress caused by cardiovascular disease.

17. The method of claim 3, wherein the oxidative stress caused by cataracts.

18. The method of claim 3, wherein the oxidative stress caused by dementia.

19. The method of claim 3, wherein the oxidative stress caused by osteoporosis.

20. The method of claim 3, wherein the oxidative stress caused by type 2 diabetes.

21. The method of claim 3, wherein the oxidative stress caused by chemotherapy.

22. The method of claim 3, wherein the oxidative stress caused by radiation therapy.

23. The method of claim 3, wherein the oxidative stress caused by hypertension.

* * * * *

UNITED STATES PATENT AND TRADEMARK OFFICE
CERTIFICATE OF CORRECTION

PATENT NO. : 10,441,578 B2
APPLICATION NO. : 15/875872
DATED : October 15, 2019
INVENTOR(S) : Louis Habash Page 1 of 2

It is certified that error appears in the above-identified patent and that said Letters Patent is hereby corrected as shown below:

In the Specification

Column 11, Line 34, delete "nixtroxide" and insert --nitroxide--.

Column 18, Line 29, delete "xeniobiotic" and insert --xenobiotic--.

Column 19, Line 61, delete "tranferase" and insert --transferase--.

Column 26, Line 29, delete "alhylhenxyl" and insert --alkylbenzyl--.

Column 28, Line 18, delete "(Nissar" and insert --Nissar--.

Column 28, Line 32, delete "(Nissar" and insert --Nissar--.

Column 34, Line 57, delete "(MM)" and insert --(MRI)--.

Column 36, Line 16, delete "trophobalstic" and insert --trophoblastic--.

Column 36, Line 21, delete "lymphangioendothelio" and insert --lymphangioendothelioma--.

Column 37, Line 51, delete "Burkitts" and insert --Burkitt's--.

Column 37, Line 53, delete "rumors," and insert --tumors,--.

Column 36, Line 58, delete "psteosarcoma," and insert --osteosarcoma,--.

Column 40, Line 50, delete "Henoch-Schoenlein purpurea" and insert --Henoch–Schonlein purpura--.

Column 40, Line 61, delete "arthopathy" and insert --arthropathy--.

Signed and Sealed this
Seventh Day of April, 2020

Andrei Iancu
*Director of the United States Patent and Trademark Office*

Column 40, Line 62, delete "colitic" and insert --colitis--.

Column 40, Line 64, delete "spondyloarthopathy," and insert --spondyloarthropathy,--.

Column 41, Line 20, delete "haemosiderosis" and insert --hemosiderosis--.

Column 41, Line 34, delete "vasulitis" and insert --vasculitis--.

Column 41, Lines 49, delete "choleosatatis" and insert --cholestasis--.

Column 42, Lines 4-5, delete "abetalipoprotemia," and insert --abetalipoproteinemia,--.

Column 42, Lines 36-37, delete "choleosatatis," and insert --cholestasis,--.

Column 43, Line 7, delete "haemosiderosis" and insert --hemosiderosis--.

Column 43, Lines 8-9, delete "Hallerrorden-Spatz disease," and insert --Hallervorden-Spatz disease,--.

Column 43, Line 10, delete "hemachromatosis" and insert --hemochromatosis--.

Column 43, Line 13, delete "purpurea," and insert --purpura,--.

Column 43, Line 31, delete "lipidema," and insert --lipedema,--.

Column 43, Lines 31-32, delete "lymphederma," and insert --lymphedema,--.

Column 43, Line 43, delete "myelodyplastic" and insert --myelodysplastic--.

Column 43, Line 50, delete "epidydimitis," and insert --epididymitis,--.

Column 44, Line 4, delete "Raynoud's" and insert --Raynaud's--.

Column 44, Line 13, delete "Sjorgren's" and insert --Sjogren's--.

Column 44, Line 16, delete "spondyloarthopathy" and insert --spondyloarthropathy--.

Column 44, Line 27, delete "thromboangitis" and insert --thromboangiitis--.

Column 44, Line 38, delete "hemaphagocytic" and insert --hemophagocytic--.

Column 45, Line 48, delete "candirect" and insert --can direct--.

Column 47, Line 42, delete "nixtroxide" and insert --nitroxide--.

Column 48, Line 28, delete "tissue tissue" and insert --tissue--.